US011324429B2

(12) United States Patent
Willis et al.

(10) Patent No.: US 11,324,429 B2
(45) Date of Patent: May 10, 2022

(54) HEADGEAR HAVING ELECTRODES INTEGRALLY FORMED THEREIN HAVING A GEL DISTRIBUTION APPARATUS

(71) Applicant: Forest Devices, Inc., Pittsburgh, PA (US)

(72) Inventors: Dan Willis, Pittsburgh, PA (US); Carmelo R. Montalvo, Pittsburgh, PA (US); Liam Berti, Havertown, PA (US)

(73) Assignee: Forest Devices, Inc., Pittsburgh, PA (US)

( * ) Notice: Subject to any disclaimer, the term of this patent is extended or adjusted under 35 U.S.C. 154(b) by 0 days.

(21) Appl. No.: 16/749,265

(22) Filed: Jan. 22, 2020

(65) Prior Publication Data
US 2020/0237248 A1    Jul. 30, 2020

Related U.S. Application Data

(60) Provisional application No. 62/798,157, filed on Jan. 29, 2019.

(51) Int. Cl.
*A61B 5/00*    (2006.01)
*A61B 5/291*   (2021.01)

(52) U.S. Cl.
CPC ............ *A61B 5/291* (2021.01); *A61B 5/0006* (2013.01); *A61B 5/6803* (2013.01); *A61B 5/6814* (2013.01)

(58) Field of Classification Search
CPC ..... A61B 5/291; A61B 5/6803; A61B 5/6814; A61B 5/316; A61B 5/369;

(Continued)

(56) References Cited

U.S. PATENT DOCUMENTS 3,508,541 A * 4/1970 Westbrook ............... A61N 1/04
                                               600/383
4,632,122 A * 12/1986 Johansson ............. A61B 5/291
                                               600/383

(Continued)

FOREIGN PATENT DOCUMENTS

CN       103720470 A     4/2014

OTHER PUBLICATIONS

International Search Report for PCT/US2020/015295 dated Apr. 30, 2020.

(Continued)

*Primary Examiner* — Joseph A Stoklosa
*Assistant Examiner* — Brian M Antiskay
(74) *Attorney, Agent, or Firm* — Buchanan Ingersoll & Rooney PC

(57) ABSTRACT

A sensor array can be integrally defined in a fabric headgear. A gel distribution module can be connected to each sensor of the sensor array. Each module can include an outer part that is connectable to a second inner part so that the fabric of the headgear and sensor are between the inner and outer parts. Each module can be configured to facilitate the distribution of a gel onto a scalp of a patient and into contact with the sensor via actuation of an actuator of the module to permit rapid deployment of the gel at the sensor specific locations on the head of a patient. The gel can be distributed directly onto skin of the scalp even when the patient has hair at the sensor location. The sensor array can be positioned so that asymmetrical positioning of the sensors on a patient's head is detectable.

14 Claims, 13 Drawing Sheets

(58) Field of Classification Search
CPC . A61B 2562/0215; A61B 5/0006; A61B 5/25; A61B 2562/164; A61B 5/24; A61B 5/7203; A61B 5/282; A61B 2562/046; A61B 5/4839; A61B 5/6831; A61B 5/6843; A61B 5/259; A61B 5/6868; A61B 2562/227; A61B 5/053
USPC .......................... 600/372, 382–393, 544–545
See application file for complete search history.

(56) References Cited

U.S. PATENT DOCUMENTS

| | | | |
|---|---|---|---|
| 5,078,134 A * | 1/1992 | Heilman | A61N 1/0492 607/4 |
| 5,479,934 A | 1/1996 | Imran | |
| 6,301,493 B1 | 10/2001 | Marro et al. | |
| 6,510,333 B1 * | 1/2003 | Licata | A61B 5/324 600/383 |
| 6,574,513 B1 | 6/2003 | Collura et al. | |
| 6,640,122 B2 | 10/2003 | Manoli et al. | |
| 10,081,486 B2 * | 9/2018 | Murray | B65D 85/72 |
| 2008/0009763 A1 * | 1/2008 | Chiou | A61B 5/25 600/373 |
| 2012/0107811 A1 * | 5/2012 | Kelso | B29C 66/84121 435/6.11 |
| 2015/0065838 A1 * | 3/2015 | Wingeier | A61N 1/0456 600/383 |
| 2016/0022165 A1 * | 1/2016 | Sackellares | A61B 5/6814 600/383 |
| 2017/0281036 A1 * | 10/2017 | Parvizi | A61B 5/325 |
| 2018/0165923 A1 * | 6/2018 | Schmit | G08B 5/36 |

OTHER PUBLICATIONS

Written Opinion of the International Searching Authority for PCT/US2020/015295 dated Apr. 30, 2020.

* cited by examiner

HEADGEAR HAVING ELECTRODES INTEGRALLY FORMED THEREIN HAVING A GEL DISTRIBUTION APPARATUS

CROSS-REFERENCE TO RELATED APPLICATIONS

This patent application claims priority to U.S. Provisional Patent Application No. 62/798,157, filed on Jan. 29, 2019. The entirety of this provisional patent application is incorporated by reference herein.

FIELD OF THE INVENTION

The present innovation relates to devices that can be utilized to measure health metrics of a patient and provide that measurement data to a computer device to facilitate diagnosis of a condition of the patient. The present innovation also relates to methods of making and using such devices. Some embodiments of the present innovation can allow for the rapid assessment of a neurological condition of a patient via a computer device connected to headgear having a sensor array that is worn by the patient to facilitate early diagnosis of a possible neurological condition (e.g. stroke), so that a patient can be quickly routed to a care facility that may be best equipped to treat that condition given the circumstances of the patient's location and medical condition.

BACKGROUND OF THE INVENTION

A fabric headband in which electrodes are in fixed positions can be used to position electrodes on the head of a patient. The electrodes are often intended to be placed so they will fall in the positions described in the 10/20 montage. The electrodes in such headgear are manually inserted as separate elements into a fabric cap that can stretch significantly so that the cap is wearable on various sized heads. Other headgear in which electrodes can be included are disclosed in U.S. Patent Application Publication Nos. 2016/0235322 and 2010/0036275. Electrode configurations and uses can also be appreciated from U.S. Patent Application Publication Nos. 2017/0281036, 2016/0346534, 2016/0287127, 2016/0144186, 2016/0022981, 2015/0313498, 2015/0112153, 2014/0142410, 2014/0243643, 2013/0023748, 2012/0143020, 2012/022349, 2011/0245707, 2010/0137708, 2007/0272313, and 2007/0255127 and U.S. Pat. Nos. 3,474,775, 3,602,216, 3,776,228, 4,458,687, 4,742,831, 4,919,148, 5,689,215, 6,516,218, 6,640,122, 6,952,605, 7,367,956, 7,474,918, 7,616,980, 7,941,213, 8,265,736, 8,444,559, and 8,663,121.

SUMMARY

Headgear and methods of using and making headgear for detection of a neurological condition of a patient are provided herein. Additionally, gel distribution modules and sensor arrays for such headgear are provided herein. A communication connection method for connecting the sensor array to a computer device is also provided.

Embodiments of the headgear can include a flexible body having a plurality of sensors defined thereon and a plurality of conductive connectors defined thereon. Each of the conductive connectors can extend from a respective one of the sensors for connection of the sensors to a computer device. The body can be structured to have a front side, a rear side opposite the front side, a left side, and a right side opposite the left side. The sensors can be defined on the front side, the rear side, the left side and the right side via screen printing or membrane overlaying.

The flexible body can be comprised of fabric or a fabric type material. The fabric or fabric type material can include polyester, cotton and polyester blended fabric, nylon, flax, rayon, viscose, material composed of regenerated cellulose fibers, wool, bamboo, texliner mesh, hemp, leather, fish leather, lyocell, or other type of fabric material or textile type material. In alternative embodiments, the body of the headgear can be composed of a semi-rigid plastic.

Embodiments of the head gear can include gel distribution modules. In some embodiments, the gel distribution modules are attached to the body so that there is a gel distribution module adjacent a respective one of the sensors of the sensor array for each and every one of the sensors.

In some embodiments, each of the gel distribution modules include a first inner part that is connectable to a second outer part. The first inner part can be attached to the body. The first inner part can be connected to the second outer part such that the first inner part is positioned between the respective one of the sensors to which the gel distribution module is adjacently positioned and the second outer part. Each of the gel distribution modules can have a gel reservoir at least partially defined via the second outer part or the second outer part and a seal member. The second outer part can be flexible so that the second outer part is moveable to change a dimension of the gel reservoir to increase a pressure within the gel reservoir to exceed a pre-selected threshold for outputting of gel from the gel reservoir to a scalp of a patient wearing the headgear via at least one hole of the first inner part that is a portion of a primary gel conduit along which the gel moves as it is expelled from the gel reservoir to be applied onto the scalp. The seal member can be connected to at least one of the first inner part and the second outer part. The seal member can be configured to move from a closed position to an open position in response to the pressure within the gel reservoir exceeding the pre-selected threshold for outputting of the gel from the gel reservoir.

In some embodiments, the seal member is only attached to the first inner part via at least one frangible connection for movement from the closed position to the open position. In other embodiments, the seal member is only attached to the second outer part via at least one frangible connection for movement from the closed position to the open position. In yet other embodiments, the seal member is attached to both the first inner part and the second outer parts. In such an embodiment, the seal member can have a frangible connection with the first inner part and/or the second outer part for movement from the closed position to the open position or can be configured to fracture into multiple pieces for movement from the closed position to the open position in response to the pressure of the gel reservoir exceeding the pre-selected threshold.

In some embodiments, each of the gel distribution modules can include a first inner part that is connectable to a second outer part. The first inner part can be positioned on an interior facing surface of the body and the second outer part can be positioned on an exterior facing surface of the body that is opposite the interior facing surface of the body. The first inner part can be connected to the second outer part such that the respective one of the sensors to which the gel distribution module is adjacently positioned is between the first inner part and the second outer part. For example, the second outer part can be snap-fit connected to the first inner part to position the body and sensor between the first inner part and second outer part.

In some embodiments, each gel distribution module can utilize a first inner part that has a hole and a second outer part the has a gel reservoir that is in fluid communication with the hole via a primary gel conduit defined between the gel reservoir of the second outer part and the hole of the first inner part. The first inner part can also have a recess and a gel distributor element that extends from the recess to a position that partially fills the primary gel conduit to direct a portion of gel that passes through the primary gel conduit into a gel chamber that is at least partially defined by the recess of the first inner part. At least a portion of the sensor can be positioned adjacent the recess such that gel that is passed within the gel chamber via the gel distributor element contacts the sensor.

The first inner part can also have at least one projection that extends away from the first inner part to contact a head of the patient when the patient wears the headgear. Each gel distribution module can be attached to the body such that the gel distribution module is manipulatable to move the at least one projection along the head of the patient to abrade skin on the scalp of the patient.

Each gel distribution module can also have a supplementary gel conduit that is at least partially defined by at least one hole in the second outer part that is spaced apart from a gel reservoir of the second outer part and is aligned with an opening of the first inner part. The opening of the first inner part can be spaced apart from a hole of the first inner part that partially defines a primary gel conduit through which gel from the gel reservoir is passable.

Embodiments of the headgear can also include at least one light emitting diode. Each light emitting diode (LED) can be connectable to a respective one of the gel distribution modules and/or to a respective one of the sensors. Each light emitting diode can be configured to emit a light to indicate the sensor to which the gel distribution module is positioned adjacent and/or to which that LED is connected has a sufficient connection to a head of the patient for use in testing of the patient.

Embodiments of the headgear can also (or alternatively) include at least one LED that is connectable to at least some of the conductive connectors to emit a light in response to an impedance difference between the conductive connectors to which the LED is connected is at or exceeds a pre-selected threshold to indicate an asymmetric positioning of the sensors of the headgear on a head of the patient.

Methods of making and using embodiments of the headgear are also provided. Embodiments of the method can include adjusting the body of the headgear to form a headgear, positioning the headgear on a patient's head for symmetric positioning of sensors of the sensor array, and connecting the sensors to a computer device for testing the patient to diagnose at least one condition of the patient (e.g. determine whether the patient has experienced a stroke, etc.). Gel distribution modules attached to the body of the headgear adjacent to the sensors can be used to apply gel to the head of the patient adjacent the sensors of the headgear before the testing occurs.

Other details, objects, and advantages of a sensor array, sensor hubs, gel distribution mechanisms, headgear, neurological condition detection device, and methods of making and using the same will become apparent as the following description of certain exemplary embodiments thereof proceeds.

BRIEF DESCRIPTION OF THE DRAWINGS

Exemplary embodiments of headgear, electrodes, sensor arrays, sensor hubs, gel distribution mechanisms, neurological condition detection mechanisms, and methods of making and using the same are shown in the accompanying drawings. It should be understood that like reference numbers used in the drawings may identify like components.

DETAILED DESCRIPTION

Figure 1:
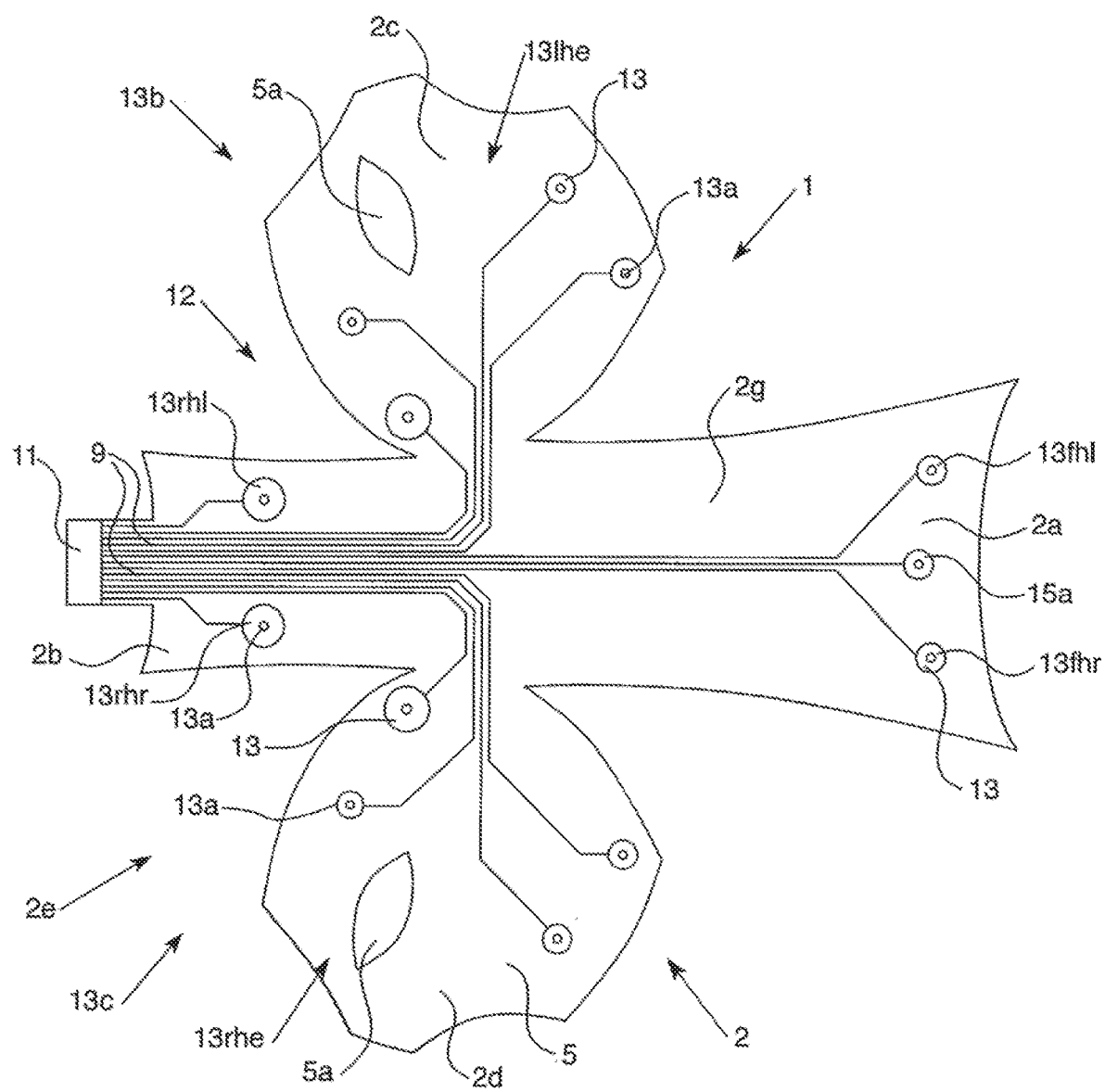
FIG. 1 a perspective view of a first exemplary body 2 of headgear 1 that can be configured to be worn on the head of a patient.

An embodiment of headgear 1 having a sensor array 12 can include a body 2. The body can be comprised of fabric or a fabric type material. For example, the body can be formed from cotton, polyester, cotton and polyester blended fabric, nylon, flax, rayon, viscose, material composed of regenerated cellulose fibers, wool, bamboo, texliner mesh, hemp, leather, fish leather, lyocell, another other type of fabric material or textile type material and combinations thereof. The body 2 can alternatively be composed of a semi-rigid plastic.

For embodiments composed of fabric or a fabric-type material, the fabric of the fabric body 2 can be a polyester (e.g. polyester threads woven together, polyester and cotton threads woven together, etc.) or other type of fabric material or fabric-type material that can facilitate the integral printing of sensors 13 and conductive connectors 9 for connecting the sensors 13 to a communication connector 11 configured to connect the sensors 13 to (i) a computer device (not shown) via a wired communication connection or (ii) a transceiver device for communicatively connecting the sensors 13 to the computer device via a wireless communicative connection (e.g. Bluetooth connection, near field communication connection, Wi-Fi connection, etc.). The conductive connectors 9 can be elongated members that have first terminal ends that are opposite their second terminal ends. The conductive connectors 9 can be comprised of a metal (e.g. silver, copper, etc.) or other conductive material (e.g. graphene).

The printing of the sensors 13 and conductive connectors 9 on the fabric body 2 can be provided via membrane overlay or screen printing. The sensors 13 and conductive connectors 9 can each be printed or overlayed onto the body 2 so that the sensors 13 and conductive connectors 9 are each comprised of a body that is composed of metal (e.g. copper, silver, etc.) or other electrically conductive material (e.g. graphene, etc.). Each sensor 13 can have a body that defines an inner hole 13a. The sensors 13 can be configured as electrodes that are capable of sensing electrical signals generated within a human brain (e.g. electrocardiogram (ECG) signals, Electroencephalogram (EEG) signals, etc.). The sensors 13 can also be configured as other types of sensors that can be configured to detect human brain activity and provide measurement data related to the detected brain activity that can be transmitted to a computer device. The size, composition and/or configuration of the sensors 13 can be adjusted to meet a particular set of design criteria for different applications.

Each of the conductive connectors 9 can be comprised of a body that is structured as an elongated member that is composed of metal or other electrically conductive material that can convey an electrical signal and/or other data from the sensor(s) 13 to which that conductive connector 9 is attached to the communication connector 11 for transmission of the signal and/or other data of a sensor 13 to a computer device. Each conductive connector 9 can have at least two terminal ends—a first terminal end and a second terminal end opposite the first terminal end.

The communication connector 11 can be attached to first terminal ends of the conductive connectors 9 adjacent to or at a rear 2b of the body 2 that is opposite the front 2a of the body 2. The communication connector 11 can be a separate element connected to first terminal ends of the conductive connectors to facilitate a connection with wiring, cabling, or other communication connection device (e.g. transceiver unit, a universal serial bus ("USB") connection, etc.). In some embodiments, it is contemplated that fabric material of the body 2 can be hardened to define the communication connector 11 at the rear 2b of the body at which first terminal ends of the conductive connectors are positioned for connection to another element. Each conductive connector 9 can be positioned on the body 2 so that its second terminal end can be connected to a respective sensor 13 (e.g. terminating at the sensor 13, conductively connected to the sensor 13, etc.).

In some embodiments the communication connector 11 can be used in conjunction with a security chip to prevent fraudulent copies of the head gear from being improperly utilized. In another embodiment the communication connection 11 can be used with a security or identification chip to prevent unauthorized use and/or record the number of uses of the sensor array 12 or headgear 1. Sterilization or other use of the headgear 1 and/or sensor array 12 can also be tracked (or can alternatively be tracked) by use of such features.

The body 2 can have a left side 2c and a right side 2d that is opposite its left side 2c. The right and left sides 2d, 2c of the body 2 can be positioned between the front 2a and rear 2b sides of the body 2. The body can also have an inward facing surface 2e and an external facing surface 2f that is opposite the inward facing surface 2e. In some embodiments, the external facing surface 2f can be considered a top surface or outer surface that can define an external surface 7a of a formed headgear 1 and inward facing surface 2e can be considered a bottom surface or an inner surface 7b of a formed headgear 1 that is opposite the external surface 7a of the headgear 1. The left side 2c and the right side 2d of the body 2 can each be structured as side portions 5 of the body 2 or be attached to a central portion of the body 2 via sewing, stapling, or other fastening mechanism in embodiments that are structured such that the entire body 2 is not formed as an integral body structure. In some embodiments, the side portions can be generally circular in shape (e.g. resembling a circle). The outer periphery of each side portion 5 can include irregular curves or other shaping to accommodate a particular design criteria so that the headgear 1 formed by the body is positionable so that the left side 2c is positioned on a left side of a patient's head and the right side is positionable on the right side 2d of a patient's head. Each side portion 5 can have a hole 5a sized so that a patient's ear can be inserted through the ear hole 5a and be positioned on an outer side of the body 2, or external surface 7a of the headgear 1.

In some embodiments, additional material, holes, sewing patterns, or other features can be added around edges of the body 2 that can be configured to make assembly of the body into headgear 1 easier and/or to reduce material bunching when the body is moved into a headgear shape (e.g. shape of a cap, a hollow-hemispherical shape, etc.). One such example of another alternative body configuration can be appreciated from FIG. 13, which illustrates a body 2 having a number of holes 2w of different shapes defined therein for the headgear 1. The body 2 can be formed so that one or more peripheral edge portions have a greater thickness to help allow a user to more easily manipulate the body and/or reduce any material bunching that can occur when the body is moved into a headgear-type shape (e.g. shape of a cap, a hollow-hemispherical shape, etc.).

The inward facing surface 2e of the body can have the sensors 13 and conductive connectors 9 positioned thereon. This can position the sensors 13 on the inner surface 7b of the headgear for contacting with the scalp S of a patient's head that is inserted into the opening 1a of the headgear 1 formed from the body 2.

The external facing surface 2f of the body can be composed of fabric or other material and not have such elements. The body can also include an inner layer between the external facing surface 2f and inward facing surface 2e. The inner layer can be composed of carbon or other insulator that may provide for noise cancellation by blocking radio frequencies from outside of the opening 1a from passing into the inward facing surface 2e and/or sensors 13. The inner insulative layer can be an electrically insulative layer that is configured to physically block all frequency ranges or can alternatively be configured to just block a particular set of frequency ranges. Such an insulative layer can be configured to provide noise cancellation by blocking of frequencies or at least one frequency range to improve the data obtained from sensors and require less data processing for use of such data. In yet other embodiments, the insulative layer can be positioned on the external facing surface 2f of the body or be formed when the body 2 is made so that the insulative layer is the external facing surface 2f of the body 2.

Figure 3:
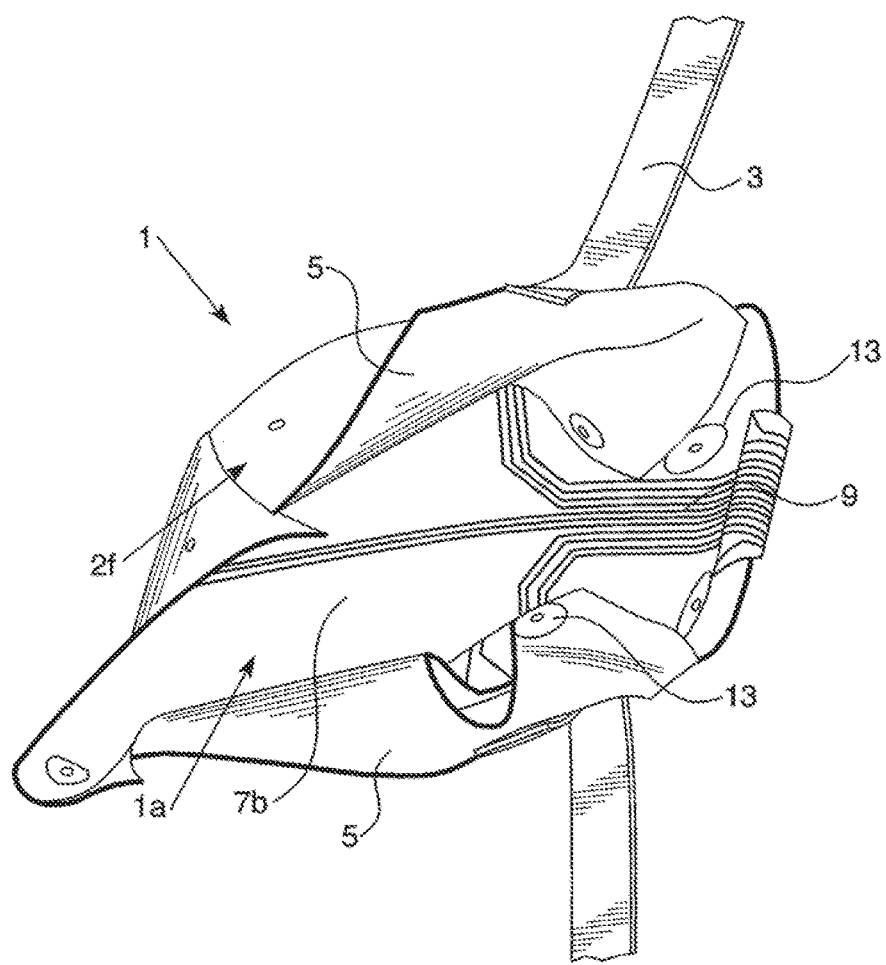
FIG. 3 is a perspective bottom view of an exemplary embodiment of the headgear 1 having an opening 1a sized for a patient's head to be positioned therein so that the headgear 1 can be worn on the patient's head.
Figure 4:
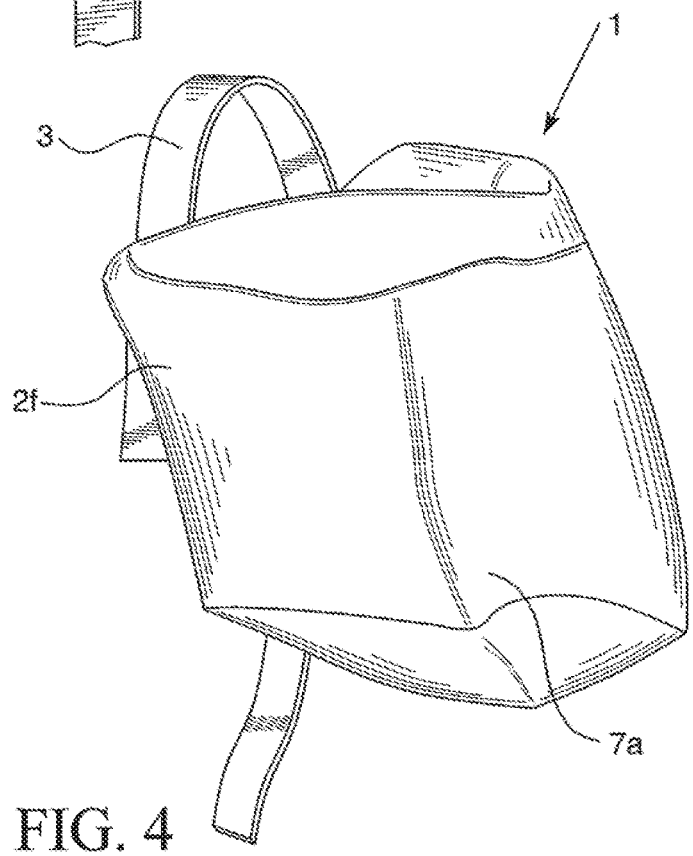
FIG. 4 is a perspective top view of an exemplary embodiment of the headgear 1.
Figure 5:
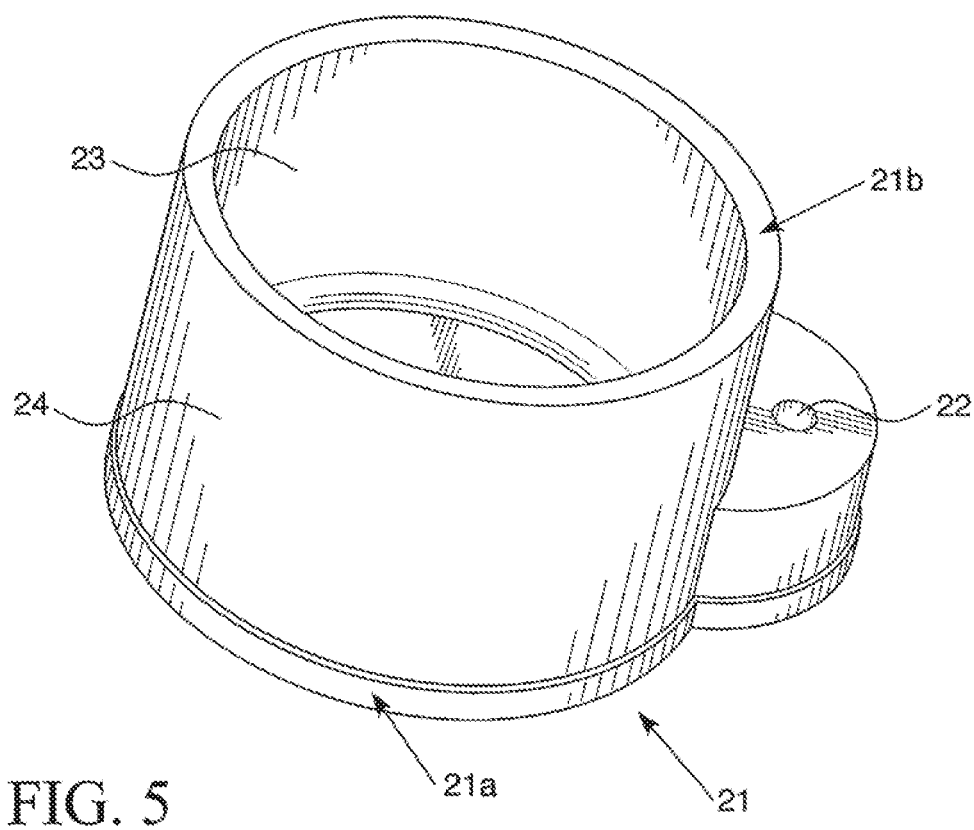
FIG. 5 is a perspective view of a first exemplary embodiment of a gel distribution module 21 having a first inner part 21a and a second outer part 21b that is connectable to a sensor 13 of the headgear's sensor array 12. An outermost portion of the module that can include an actuator 21c is cut away to illustrate the gel reservoir 23 defined in the second outer part 21b of the module.
Figure 6:
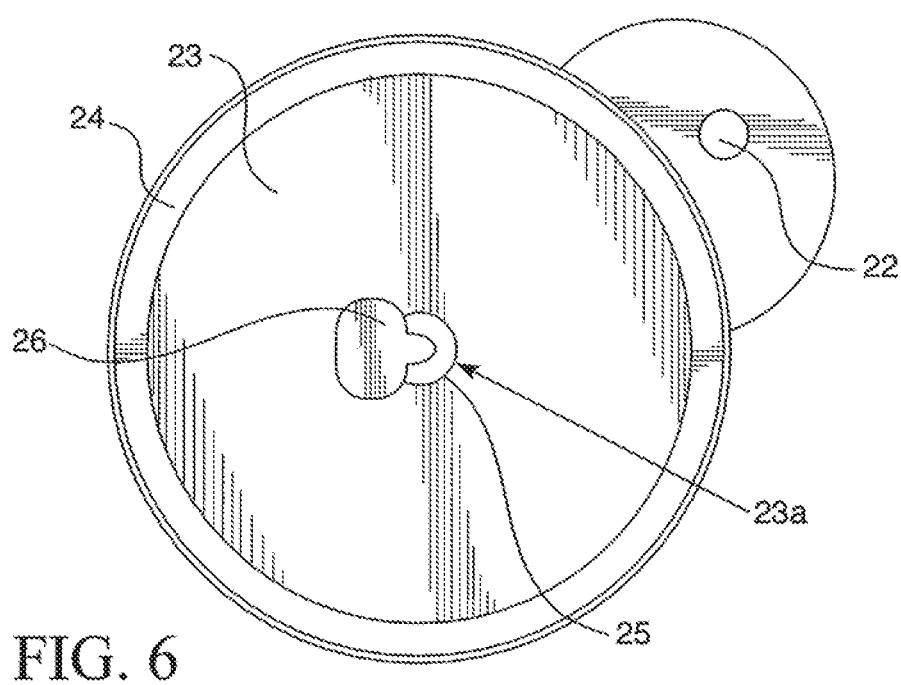
FIG. 6 is a top view of the first exemplary embodiment of the gel distribution module 21 shown in FIG. 5.
Figure 7:
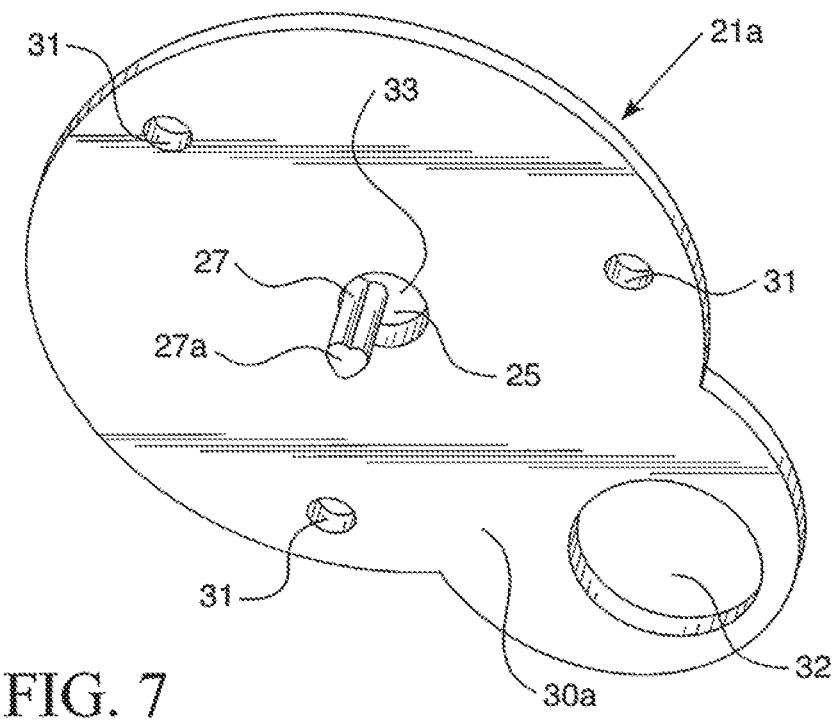
FIG. 7 is a bottom perspective view of the first inner part 21a of the first exemplary embodiment of the gel distribution module 21.
Figure 8:
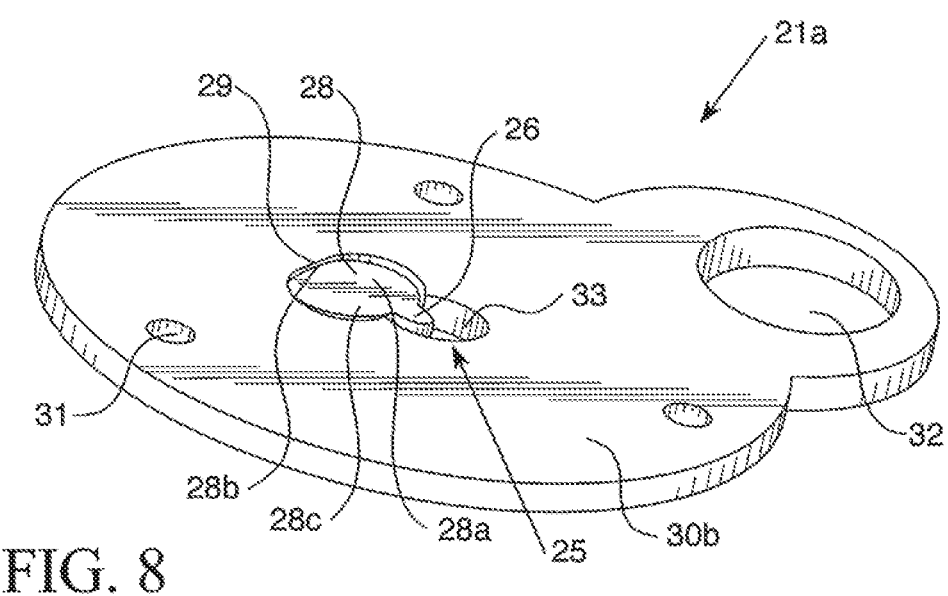
FIG. 8 is a top perspective view of the first inner part 21a of the first exemplary embodiment of the gel distribution module 21.
Figure 9:
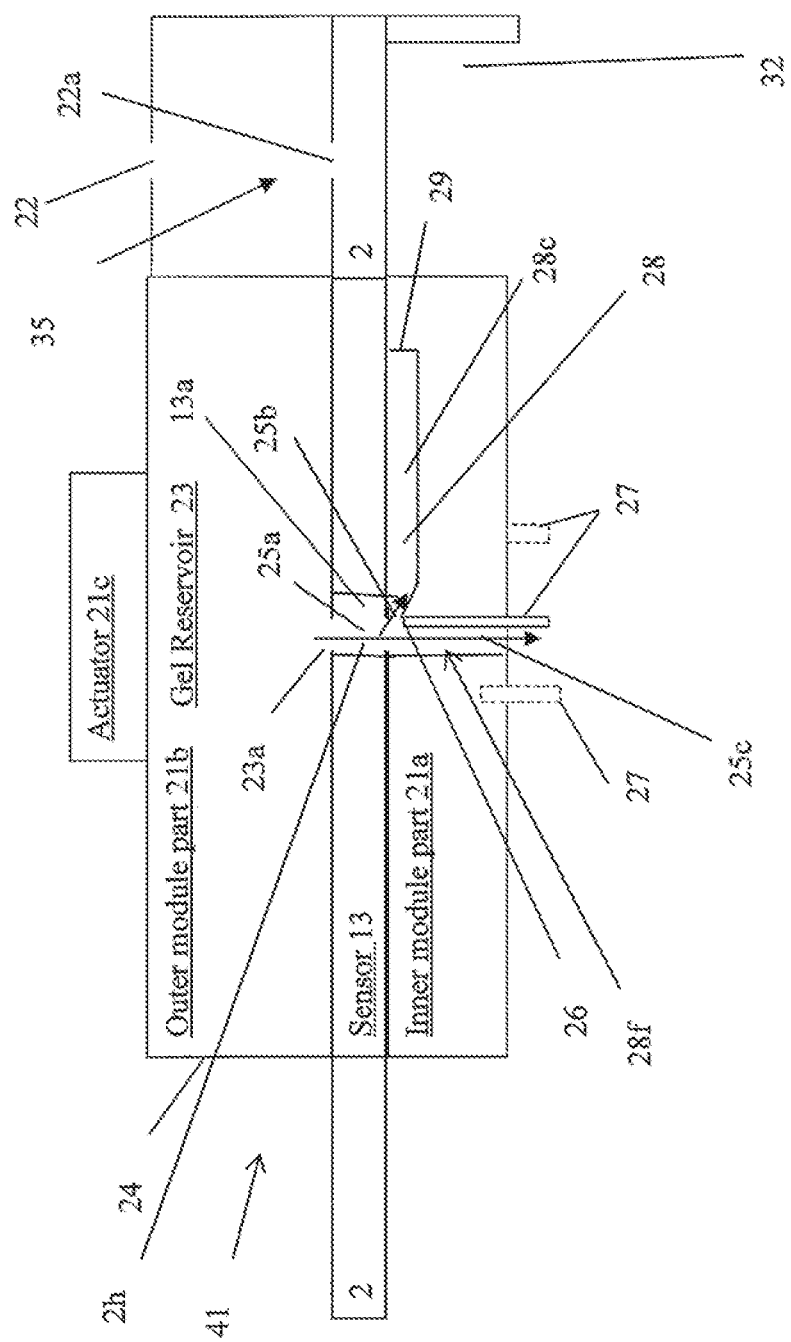
FIG. 9 is a schematic view of an exemplary hub 41 of the sensor array 12 utilizable in embodiments of the headgear 1 in which an exemplary embodiment of the gel distribution module 21 is attached to the headgear 1 adjacent the sensor 13 for gel distribution to the sensor 13 and patient's head (e.g. skin of the scalp of the patient) after the headgear 1 is properly positioned on the head of a patient.
Figure 13:
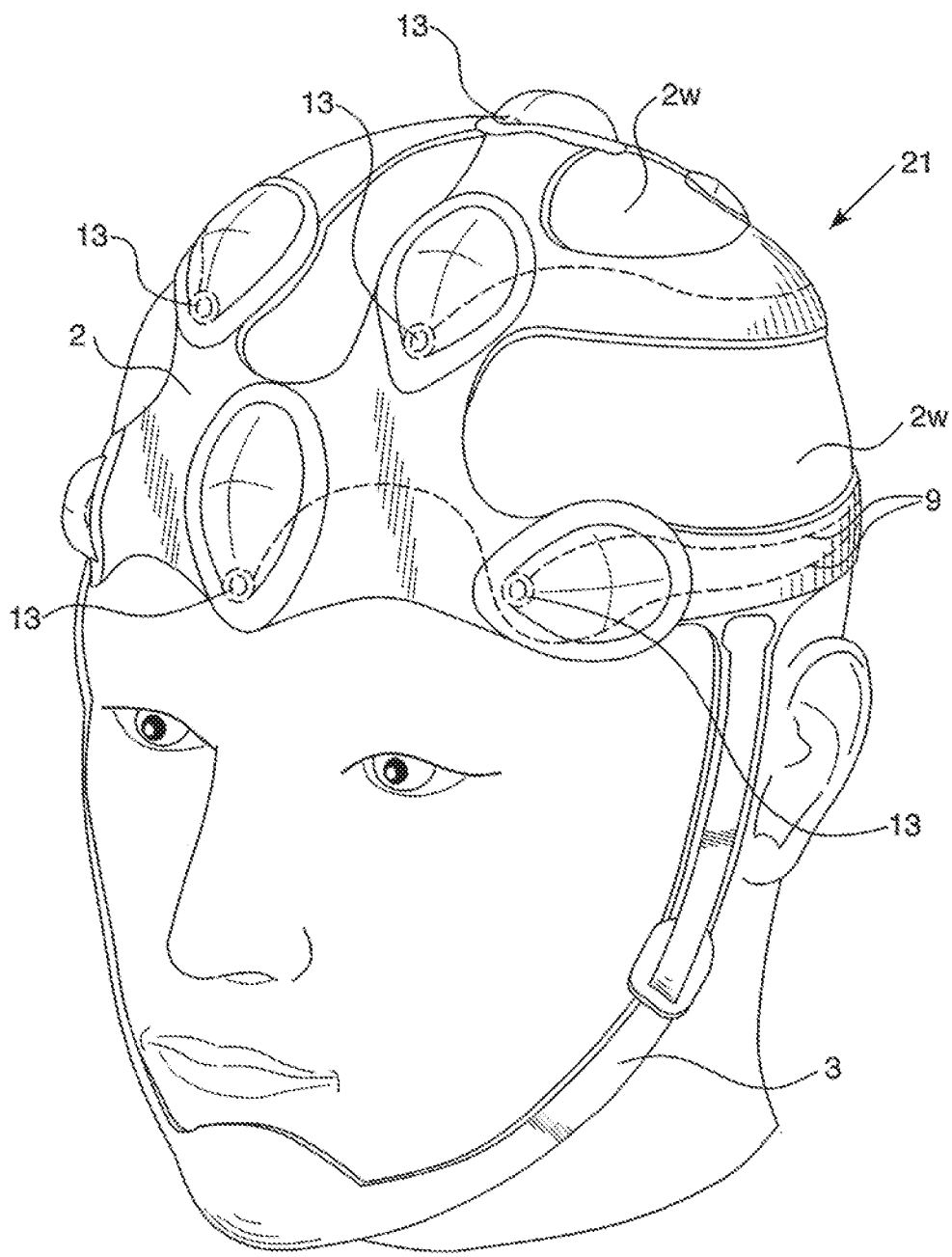
FIG. 13 is a perspective view of another exemplary embodiment of headgear 1 that can be configured to be worn on the head of a patient having gel distribution modules 21.
Figure 14:
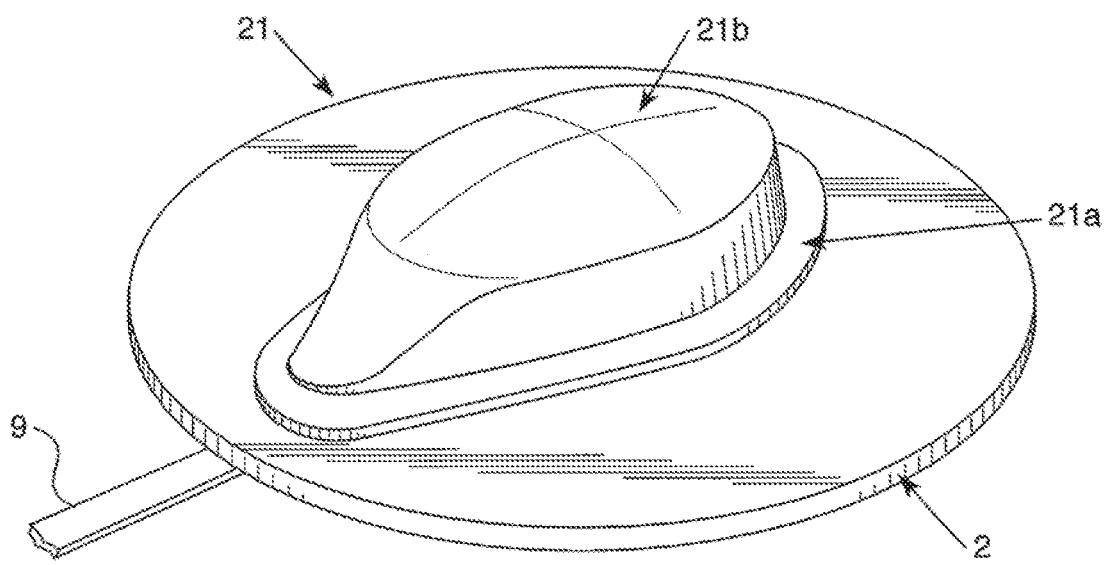
FIG. 14 is a fragmentary view of the headgear shown in FIG. 13 to better illustrate an exemplary gel distribution module utilized in the headgear 1.
Figure 15:
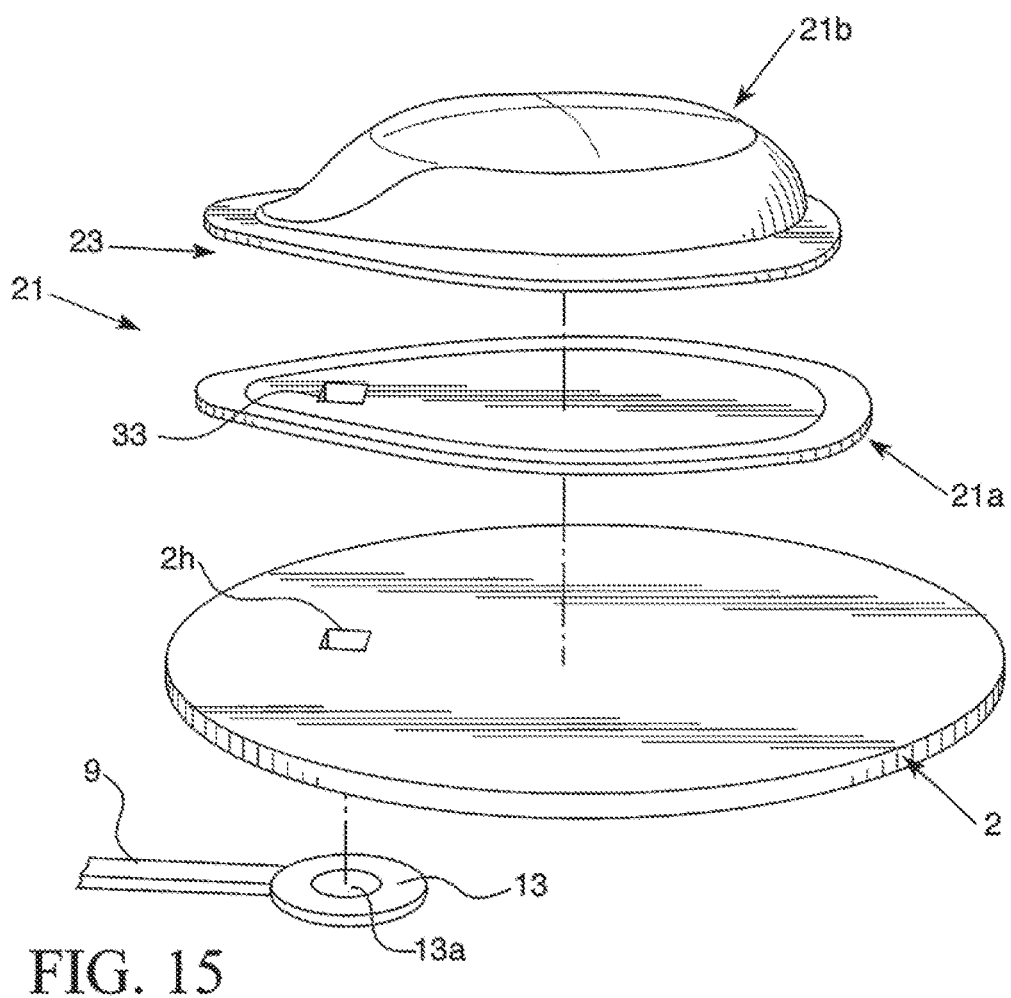
FIG. 15 is an exploded view of the exemplary gel distribution module utilized in the headgear 1 shown in FIG. 13.
Figure 16:
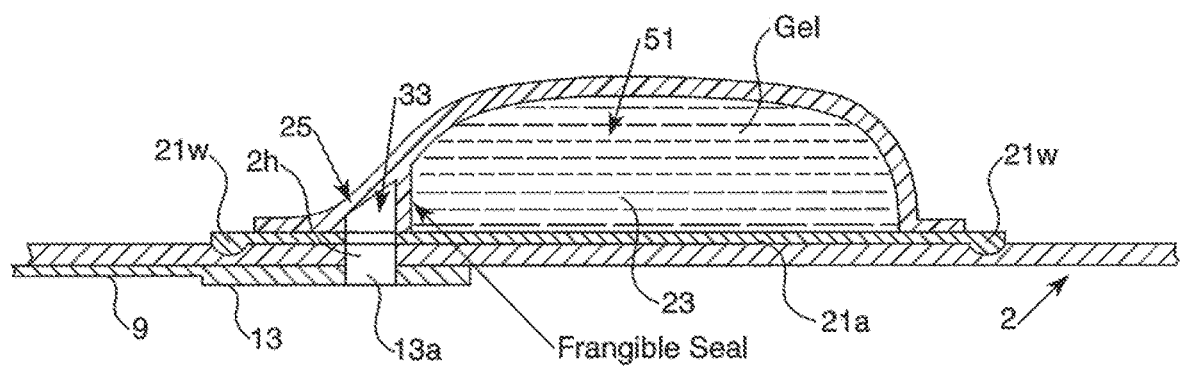
FIG. 16 is a cross-sectional view of the exemplary gel distribution module shown in FIG. 14 while the module is in a filled and non-actuated state.

The body 2 can be structured so that the body 2 is adjustable into a headgear structure that can have a defined opening 1a for receiving the head of a patient so the patient can wear that headgear on his or her head. For example, the body can be deformable and/or flexible and/or bendable to accommodate the formation of a bowl-like shape, a hollow sphere-like shape or hollow hemisphere-like shape. FIGS. 3 and 4 illustrate on example of a hollow hemisphere-like shape, or bowl-like shape. FIG. 13 illustrates another example of a hollow bowl-like shape or hemisphere-like shape having holes 2w.

The body 2 can also have outer portions that are releaseably connected to an inner central portion having the sensor array 12. Each outer portion can be independently separable form an inner portion between the central portion having the sensor array 12 and that outer portion. The inner-most outer portion can be separably attached to the central portion having the sensor array 12. Each outer portion that is releaseably or separably attached can be separated without the use of a mechanical tool via the defining of a frangible connection via stitching or other type of releaseable connection (e.g. snap connections, zipper connection, etc.).

In some embodiments, the headgear 1 that is formed via deformation, flexing, and/or bending of the body 2 can be a cap or cap-like structure. The left and right sides 2c and 2d of the body 2 can each define an ear opening 5a so that a user's ear can be positioned through the ear hole 5a. At least one chin strap 3 can be attached to the left side 2c of the body 2 and at least one chin strap 3 can be attached to the right side 2d of the body to facilitate tightening the headgear 1 on the patient's head once the patient's head is in the opening 1a and being worn by the patient. For instance, after the headgear 1 is on the patient's head, and the patient's left and right ears passed through the ear holes 5a of the left and right sides 2c and 2d of the body 2, the chin strap(s) can be tied or otherwise manipulated to tightly position the chin strap(s) 3 under the patient's chin to ensure a tight top-to-bottom fit of the headgear 1 on the patient's head positioned in the headgear's opening 1a. This tightening can help position the sensors 13 so the sensors 13 can contact the patient's head and/or skin of the scalp.

The body 2 can also be structured so that a drawstring or cord can pass from the left side 2c to the right side 2d. A portion of this drawstring or cord can be positioned within the body at the rear side 2b of the body as it extends from the left side 2c to the right side 2d. In other embodiments, there may be two cords—one positioned in the left side 2c and one positioned in the right side 2d of the body that extend from these sides of the body for tightening the rear, left, and right sides of the body about the patient's rear, left and right sides of the head. Such tightening can occur by ends of the cords or opposite ends of a continuous drawstring being tightened and/or tied for positioning the tied cords or drawstring on the external surface 7a of the headgear 1 adjacent the forehead of a patient wearing the headgear 1. This type of circumferential tightening can help provide a tighter fit of the headgear along the rear, left, right, and front sides of the body 2. The circumferential tightening can help position sensors 13 on these sides of the body in better contact with the head and/or skin of the scalp when the patient is wearing the headgear 1. It should be appreciated that this circumferential type tightening can work in conjunction with the top-to-bottom tightening that can be provided via the chin strap(s) 3, which can help position the central portion 2g of the body 2 that is located between the front and rear sides 2a and 2b and also between the left and right sides 2c and 2d so that any sensors 13 that may be on the central portion 2g can be brought into a better position via use of the chinstrap(s) 3 discussed herein as well. The circumferential and/or top-to-bottom tightening can also help ensure that the position of the headgear 1 on the patient's head is maintained to keep the sensors 13 in a desired orientation and position adjacent and/or on the patient's head.

The sensors 13 of the sensor array 12 can be positioned on the inward facing surface 2e of the body 2 so that there are at least two sets of sensors—a first set of left side sensors 13b and a second set of right side sensors 13c. Each sensor 13 in the first left side sensors 13b can be positioned to correspond with a position of a respective sensor 13 of the second right side 13c sensors. The sensors 13 of the first and second sets of sensors can be arranged to provide a symmetrical positioning of sensors so that the left side sensors correspond with and match up to the right side sensors.

Figure 2:
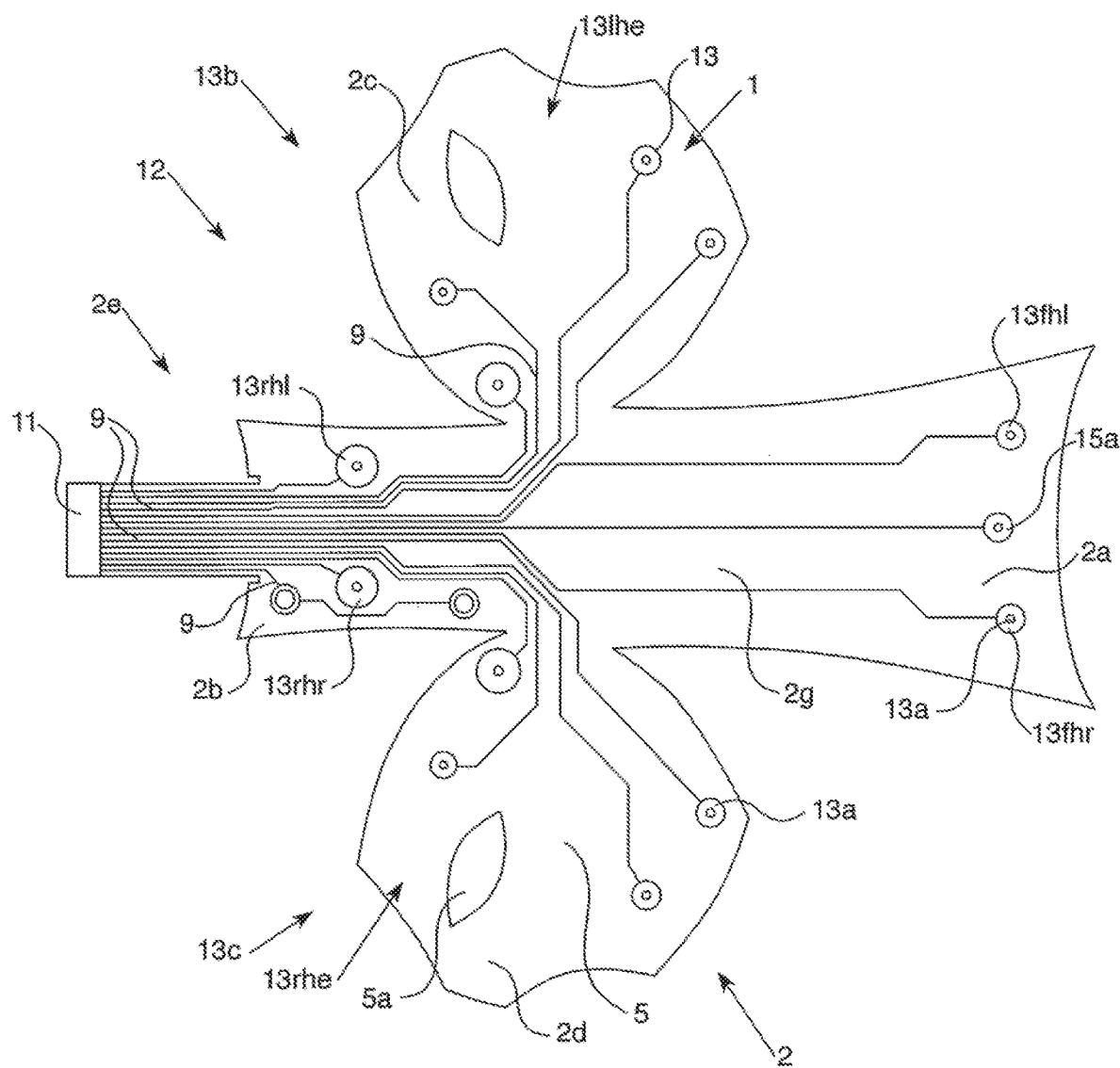
FIG. 2 is a perspective view of a second exemplary body 2 of headgear 1 that can be configured to be worn on the head of a patient.

The first set of left side sensors 13b can include at least the following sensors: a first forehead left sensor 13fhl positioned on a left side of the front 2a of the body for positioning on or adjacent a left side of the forehead of a patient who may wear headgear 1, a second rear head left sensor 13rhl positioned on a left side of the rear 2b of the body for positioning on a left side of the rear part of the head of patient who may wear headgear 1, and a plurality of spaced apart third left side sensors 13lhe positioned on the left side 2c of the body for positioning in locations on the head of the patient around the left ear of a patient who may wear the headgear formed via the body 2. The second set of right side sensors 13*c* can include at least the following sensors: a first forehead right sensor 13*fhr* positioned on a right side of the front 2*a* of the body 2 for positioning on or adjacent a right side of the forehead of the patient who may wear the headgear, a second rear head right sensor 13*rhr* positioned on a right side of the rear 2*b* of the body 2 for positioning on a right side of the rear of the patient's head when the patient wears headgear 1, and a plurality of spaced apart third right side sensors 13*rhe* positioned on the right side 2*d* of the body 2 for positioning in locations around the right ear of a patient who may wear the headgear formed via the body 2. The positions of the left side sensors in and/or on the body can correspond with locations of the right side sensors so that the left side sensors are symmetrically positionable on the head of a patient with their corresponding right side sensors. For example, the position of the first forehead right sensor 13*fhr* can be an equidistant location from a front reference sensor 15*a* that is at a center of the front 2*a* of the body 2 as the position of the first forehead left sensor 13*fhl*. The location of the second right rear head sensor 13*rhr* can be positioned to be the same distance from a center of the body as the second left rear head sensor 13*rhl*. The third left side sensor 13*lhe* can each be positioned on a left side 2*c* at a location that corresponds to a location on the right side 2*d* of the body that a respective one of the right side sensors 13*rhe* is positioned so that each corresponding pair of left and right side sensors 13*rhe* and 13*lhe* is an equidistantly spaced from a center of the body 2. In the exemplary embodiments shown in FIGS. 1 and 2, it should be appreciated that there is one pair of corresponding forehead sensors—first forehead right sensor 13*fhr* and first forehead left sensor 13*fhl*, and one pair of corresponding rear head sensors—first left rear sensor 13*rhl* and second right rear head sensor 13*rhr*, and four pairs of third left and right side sensors 13*lhe* and 13*rhe*. The embodiment of FIG. 13 can utilize the same type of sensor arrangement as well.

Other embodiments of the body 2 can utilize a different number of pairs of sensors (e.g. more than one pair of forehead and/or rear head sensors, less than four pairs or more than four pairs of left and right side sensors to be positionable adjacent the ears of a patient, one or more pairs of sensors to be positioned along a top of the head of the patient adjacent left and right sides of the top of the patient's head at positions equidistant from the center of the top of the patient's head, etc.). Additionally, the size of the sensors 13 can be modified from the embodiments shown in FIGS. 1 and 2 to adjust the density of sensors 13 located in any particular part of the body 2. Smaller sensors can be used to provide a higher density of sensors in particular regions (e.g. more sensors 13 in at least one particular area of the body 2). Larger sensor can also (or alternatively) be used to provide a lower density of sensors 13 in particular regions (e.g. less sensors in at least one particular area of the body 2). As yet another option, less or more total sensors 13 can be included in the sensor array 12 for providing a set of corresponding pairs of left side and right side sensors.

There may also be at least one reference sensor of the sensor array that is part of a third set of one or more sensors. The reference sensor can be positioned along a midpoint or center-line of the patient's head. Reference sensor 15*a* is an example of such a reference sensor, which in the embodiments shown in FIGS. 1 and 2 and is positioned at a center of the front 2*a* of the body. The reference sensor 15*a* is positioned on the body 2 for placement adjacent the center of a patient's forehead (e.g. a position centered between the patient's right and left sides of the patient's forehead) when headgear 1 is on a patient's head within the opening 1*a* of the headgear 1). More than one reference sensor can be used in some embodiments. Each such reference sensor may be at a center location on the body adjacent central portion 2*g*, rear 2*b*, or front 2*a*.

In some embodiments single or multiple snap connectors can be added as part of the sensor array 12 to connect to an external device or other type of external element. For example, a snap connector can be positioned near each ear hole 5*a* that is configured to provide an ear clip connection to a clip worn on the patient's ear. As another example, interlockable releasable connectors (e.g. snap-fit connectors, releaseable attachment fastening mechanisms, etc.) can be positioned on the body 2 to provide for connections to devices or connection mechanisms external to the headgear 1 (e.g. at least one device worn on a patient's ears or shoulders, etc.).

The external facing surface 2*f* of the body can be colored to define a centerline that extends from the rear side 2*b* to the front side 2*a* along a middle, or center, of the headgear 1 to help a user identify a proper placement of the headgear on the patient's head. A second and/or third strip can be attached to the front and/or rear sides that extend horizontally to also help guide symmetrical placement of the sensors 13 via proper positioning of the headgear 1 on the patient's head. An example of such strips and centerline can be appreciated from U.S. patent application Ser. No. 16/035,756. The entirety of U.S. patent application Ser. No. 16/035,756 is incorporated by reference herein. The computer device (not shown) to which the sensors 13 of the sensor array 12 are connectable can also be configured to determine whether the sensors of the first and second sets of sensors are properly positioned for symmetrical measurements of the left and right sides of the patient's head and provide at least one indication to a user.

In some embodiments, at least one light emitting diode (LED) can be connected to the headgear and communicatively connectable to the computer device to emit a particular color to indicate proper positioning and to emit a second color to indicate a correction to the positioning of the headgear 1 is needed for symmetrical placement of the sensors 13. The computer device can also utilize a sensor map indicator or other type of indicator as disclosed, for example, in U.S. patent application Ser. No. 16/035,756 to provide indications concerning sensor placement and positioning.

The headgear 1 can also include a hub 41 configuration at each sensor location. Each hub 41 can include a sensor 13 and a gel distribution module 21 connected to the sensor 13. The hub 41 can also include an actuator 21*c* that can be manipulated by a user or be manipulated via the computer device (not shown) being communicatively connected to the actuator 21*c* to cause gel retained in the gel reservoir 23 to be passed out of the gel reservoir 23 defined by at least one sidewall 24 of a second outer part 21*b* of the gel distribution module 21 to the sensor 13 and the scalp of a patient wearing headgear 1 via a first primary gel conduit 25 defined by the first inner part 21*a* and/or second outer part 21*b* of the gel distribution module. An example of such an actuator 21*c* can be a deformable cap that can be pressed into the gel reservoir by use of a user's finger or a mechanical tool to push the deformable cap into the gel reservoir and drive fluid out of the reservoir 23 and through the first primary gel conduit 25. Another example of such an actuator may be a mechanically moveable piston or other fluid driving mechanism attached to a portion of the gel reservoir that is moveable to drive fluid out of the gel reservoir 23 and through the first primary gel conduit 25.

The second outer part 21b can also include structure that defines or at least partially defines a second supplementary gel conduit 35 for a user to be able to insert a needle within at least one supplementary hole 22 defined in the second outer part at a location spaced apart from the gel reservoir 23. The supplementary hole 22 can be sized to facilitate insertion of a needle into a supplementary gel conduit 35 that is in communication with another hole 22a of the second outer part 21b that is aligned with an opening 32 defined in the first inner part 21a to facilitate insertion of a needle of an injector through the supplementary gel conduit 35 for injecting gel onto the scalp of the patient near the location of the sensor 13. If supplemental gel beyond what is stored in the gel reservoir 23 is needed for a particular use of the headgear 1, a user can insert a needle through holes 22, 22a, and opening 32 that help define the supplementary gel conduit 35 to inject additional gel onto a patient's head.

It should be appreciated that the first inner part 21a of the gel distribution module can be shaped to include the opening 32 that can be aligned with holes 22 and 22a for the supplementary gel conduit 35 to facilitate the positioning of the supplementary gel through the headgear 1 and onto the patient's head via a needle of an injector or other injection mechanism. The opening 32 can be defined in the first inner part 21a so that it is spaced apart from a hole 33 defined in the first inner part 21a that can be in fluid communication with the gel reservoir 23 and can help define the first primary gel conduit 25.

The hub 41 can also include an indicator LED that is configured to emit a particular colored light to indicate the sensor is properly positioned on a head of the patient to record a patient's brain activity (e.g. an EEC signal or an ECG signal). The hub can also (or alternatively) include an LED that is configured to emit a first particular colored light (e.g. green) to indicate that the sensors of the first and second sets of sensors are symmetrically positioned and emit a second colored light (e.g. red) to indicate improper asymmetric positioning of the sensors 13. An example mechanism and exemplary methodology for detection of asymmetric positioning is discussed further herein. For embodiments that include indicator LEDs, the LEDs of each hub 41 can be connected to a part of the gel distribution module 21 or to another element of the hub 41 to position the LEDs on the external surface 7a of the headgear 1.

FIGS. 5-9 help illustrate an exemplary gel distribution module 21 that can be included at each sensor 13 of the sensor array 12 of the headgear 1. The module can be configured so that a first inner part 21a is positioned close to the body 2 of the headgear 1 than a second outer part 21b. For example, the first inner part 21a can be positioned on the inner surface 7b of the headgear 1 adjacent a sensor 13 and a second outer part 21b is positioned on the external surface 7a of the headgear 1. As another example, the first inner part 21a can be positioned to directly contact the exterior surface 7a of the headgear 1 and the second outer part can be attached to the first inner part 21b so that the first inner part 21a is positioned between the body 2 of the headgear 1 and the second outer part 21b.

The positioning of the first inner part 21a can space the sensor 13 from direct physical contact with the scalp of a patient, but can be configured to facilitate an electrically conductive connection with the scalp of the patient via conductive gel and also a composition of the inner part 21a and/or a composition of a coating, or covering, of the inner part 21a. The first inner part 21a can be configured to make direct physical contact with the skin of the scalp of the patient wearing headgear 1 via at least one projection that extends from the first inner part 21a, which can help facilitate the electrically conductive connection between the scalp of the patient and the sensor 13 to which the first inner part 21a is connected.

The first inner part 21a of the module can include a series of connection holes 31 that are shaped and defined to interlockingly mate with interlocking members that extend from the second outer part 21b. The interlocking members can be configured to be extendable through the body 2 from the external surface of the body and into the connection holes 31 when the first inner part 21a is positioned on the inwardly facing surface 2e of the body to snap-fit onto the first inner part via insertion into these connection holes 31 for connecting the first inner part 21a to the second outer part 21b. Such a connection can position the body 2 between the first inner part 21a and the second outer part 21b and a sensor 13 between the first and second inner parts 21a and 21b.

The first inner part can have a first surface 30a and a second surface 30b opposite the first surface 30a. The second surface 30b can be an outwardly facing surface that faces a direction that is opposite the direction to which the first surface 30a faces. The first surface 30a can be a surface that is positioned to face toward a patient's head when the patient's head is in opening 1a of the headgear 1. At least one projection 27 can extend from the first surface 30a to project further toward the patient's scalp for contact with the patient's scalp. Each projection 27 can be sized and shaped to be extendible through hair a patient may have on the patient's head so that a distal end 27a of the projection can physically contact the skin of the scalp of a patient.

The second surface 30b of the first inner part 21a can be structured to define a recess 28 defined by at least one sidewall 29 that extends between the second surface 30b and a recessed inner surface 28a spaced from the second surface 30b via a gap 28b defined by the recess sidewall 29 that extends from the surface 28a of the recess 28 to the second surface 30b to define a gel chamber 28c between the sensor 13 and the first inner part 21a for collecting a portion of the gel passed through the primary gel conduit 25 for contacting the gel with the sensor 13. The first inner part 21a can include a gel conduit hole 33 that helps define a part of the primary gel conduit 25. A portion of the first inner part 21a that defines the surface 28a of the gel chamber 28c can extend from the gel chamber 28c into the gel conduit hole 33 to define a gel distributor element 26. The gel distributor element 26 can be positioned to partially fill part of hole 33 and first primary gel conduit 25 to contact gel passed through the first primary gel conduit 25 and direct a portion of this gel into the gel chamber 28c to fill that chamber with gel.

For example, gel passed from the gel reservoir 23 through the primary gel conduit 25 via actuator 21c can move along a gel pathway 25a defined by the primary gel conduit 25. The gel distributor element 26 can direct a portion of the gel moving along gel pathway 25a so that this directed portion of the gel moves along directed gel pathway 25b into the gel chamber 28c for contacting the sensor 13. The remaining portion of the gel is passable along the gel conduit 25 along the skin contacting pathway 25c for being directed onto the skin of the scalp of a patient. A portion of the gel from the gel reservoir may be retained in the gel conduit 25 so that there is gel that extends from the sensor 13 in the gel chamber 28c to the skin on the scalp of a patient via the conduit 25. The presence of the gel can help enhance an electrical connection the sensor 13 may have with the patient's head to provide an improved ability to detect brain activity of the patient (e.g. via EEC signals, ECG signals, etc.).

The gel can be an electrical conduction enhancement gel that can be composed to help facilitate an electrically conductive connection between a patient's scalp and the sensor 13 positioned in the gel chamber 28c via the attachment of the first inner part 21a to the second outer part 21b adjacent to the sensor 13. For example, the gel can be a silver chloride gel (e.g. an AgCl gel, a mixture that includes AgCl and water that forms a gel or slurry at room temperature, etc.). The gel could alternatively be another type of electrical conduction connection enhancement gel.

One or more projections 27 can extend from the first inner part 21a to contact the skin of a patient. A user can manipulate the second outer part 21b on the outside surface of the headgear 1 to rotate or otherwise move the gel distribution module 21 to cause the projections to be dragged along the scalp of a patient wearing headgear 1 on his or her head to rough up, or abrade, the skin of the patient's scalp. This abrasion can provide additional surface area adjacent the sensor 13 to facilitate receipt of the gel to be distributed onto the patient's head to help the gel be positioned at the desired location. This abrading can help reduce an amount of gel needed to provide an enhanced electrically conductive connection between the sensor 13 and the patient's scalp. The gel passed out of hole 33 and out of the primary gel conduit 25 can contact the projection(s) 27 and also coat the projection(s) to further facilitate the electrical connection between the patient's scalp and the sensor 13.

The first inner part 21a can also be composed of a material to help facilitate an electrically conductive connection between the sensor 13 and the scalp of a patient. For instance, the first inner part 21a can be composed of polymeric material and be coated with a silver or silver chloride coating so that the first inner part is electrically conductive. For instance, the projection(s) 27 and body of the first inner part that defines hole 33 and recess 28 can have such a coating. As another example, the first inner part 21a could be composed of an electrically conductive metal (e.g. copper, silver, etc.). The second outer part 21b could be composed of the same material as the first inner part 21a. But, because the second inner part 21b is external to the sensor 13, it can also be composed of a less expensive material (e.g. just a polymeric material) and not include the sliver or silver chloride coating that the first inner part 21a may have.

Figure 10:
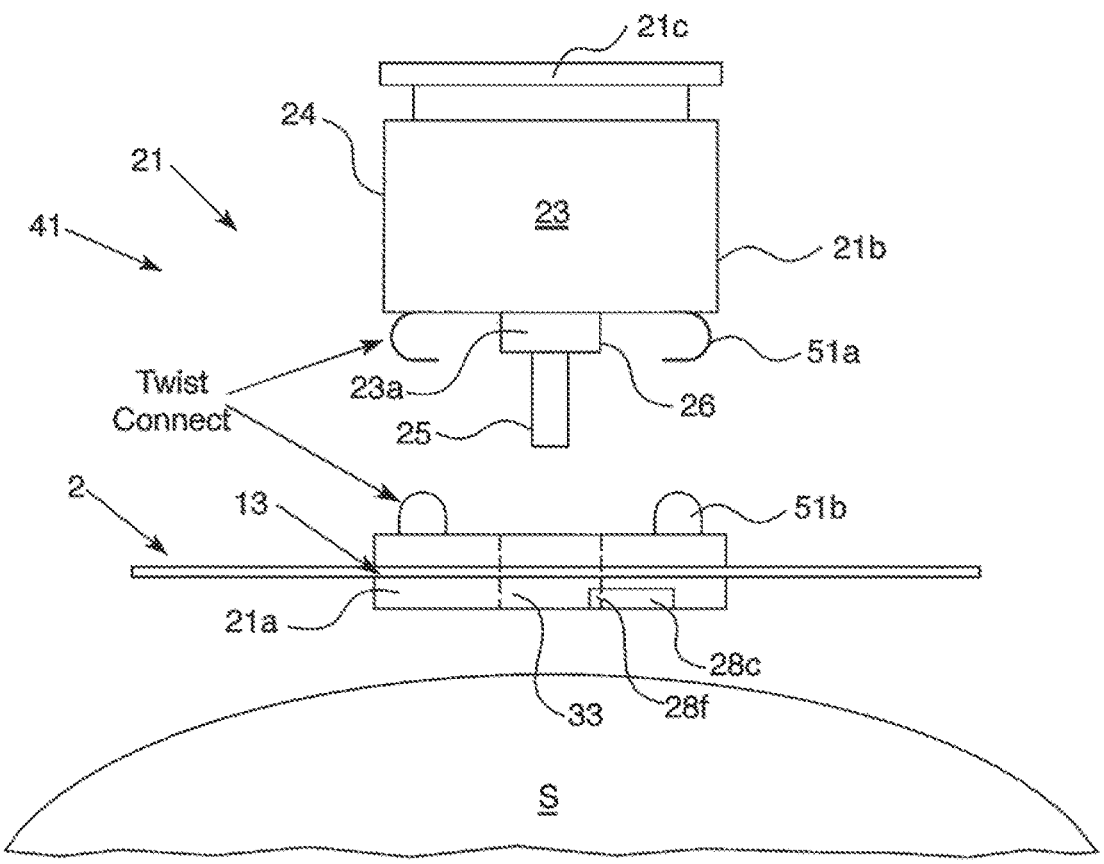
FIG. 10 is a schematic view of a second exemplary gel distribution module that is utilizable in embodiments of headgear 1.
Figure 11:
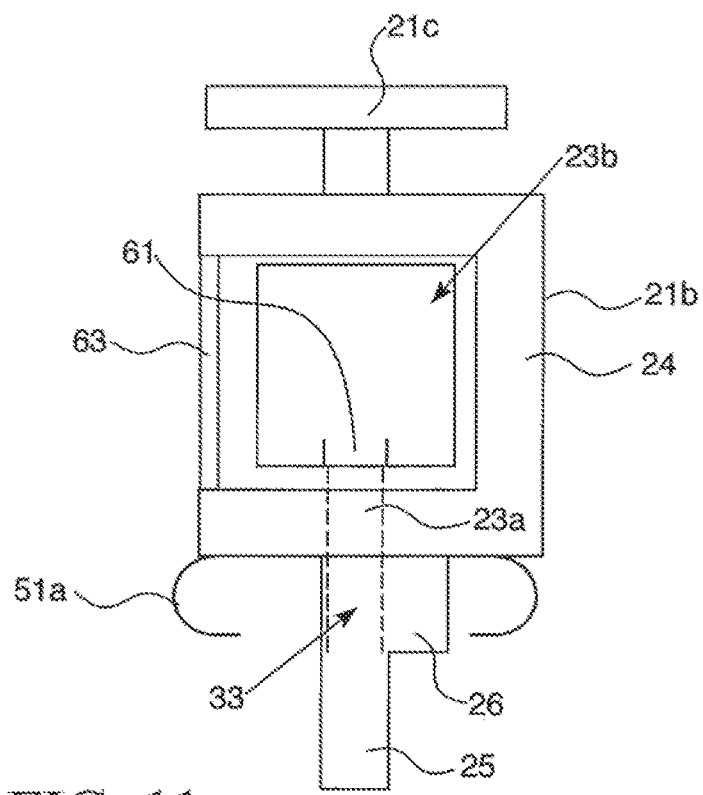
FIG. 11 is a schematic view of a third exemplary gel distribution module that is utilizable in embodiments of headgear 1.

It should be appreciated that embodiments of gel distribution modules 21 can have different configurations for use in connection with different design criteria or use methodologies. For example, referring to FIGS. 10-12, gel distribution modules 21 can have different outer part 21b configurations and inner part 21a configurations. The gel distribution modules 21 can be sized and configuration to work in conjunction with different types of sensor array 12 configurations.

For example, a gel distribution module 21 can include a gel reservoir 23 positioned within at least one external sidewall 24. A first primary gel conduit 25 can extend from adjacent the gel reservoir 23 for positioning through a hole 13a of a sensor 13 or gap 13b between two spaced apart sensors 13 or sensor portions and also a hole 33 or passageway 28f defined in a first inner part 21a attached to the body 2 adjacent the sensor(s) 13 for contacting a patient scalp S and/or head. The gel reservoir 23 can be in communication with a gel reservoir outlet 23a that is in fluid communication with the first primary gel conduit 25 so that gel is passable out of the gel reservoir and into the primary gel conduit 25 and/or the gel chamber 28c of the first inner part 21a. The gel distributor element 26 can be a part of the primary gel conduit 25 and/or be a part of the first inner part 21a that can extend from adjacent the gel chamber 28c.

The first inner part 21a can be configured so that it is permanently attached to the body 2 of the headgear so that a sensor 13 or multiple spaced apart sensors 13 that define a gap 13b between the sensors is positioned between opposite ends and/or opposite sides of the first inner part 21a. The first inner part 21a can have twist connector elements 51b that are configured to releaseably interlock with twist connector elements 51a of the second outer part 21b. For example, the second outer part 21b can have twist connector elements 51a that extend from the second outer part 21b for receipt within receptacle twist connector elements 51b of the first inner part 21a that are positioned adjacent an external surface of the body 2. As another example, the first inner part 21a can have twist connector elements 51b that extend from the first inner part 21a for receipt within receptacle twist connector elements 51a that are positioned on the second outer part 21b (e.g. defined in a sidewall 24, attached to a sidewall or other portion of a housing of the second outer part 21b, etc.). The twist connector elements can work so that a rotation of the second outer part can result in a connection being formed between the twist connector elements 51a and 51b for connecting the second outer part 21b to the first inner part 21a so that the primary gel conduit 25 passes through the hole or passageway 28f defined in the first inner part 21a that can be in fluid communication with the gel chamber 28c defined in the first inner part that is in fluid communication with at least one of the sensors 13 positioned at least partially within the first inner part 21a. For example, the gel chamber 28c can be defined so that all the sensors 13 positioned at least partially within the first inner part 21a and/or positioned entirely within the first inner part 21a are able to contact gel within the gel chamber 28c when the gel chamber is filled with gel from the gel reservoir 23 via the primary gel conduit 25 and at least one gel distributor element 26.

After the first inner part attached to the body 2 is connected to the second outer part 21b via the twist connector elements 51a and 51b, the user can manipulate actuator 21c to cause fluid from the gel reservoir 23 to pass through gel reservoir outlet 23a and into the first primary gel conduit 25 and the gel chamber 28c for applying gel to the sensor 13, first inner part 21a and scalp of a patient's head adjacent the one or more sensors positioned at least partially within the first inner part 21a. The gel can help facilitate an electrically conductive connection between the one or more sensors 13 and the scalp of the patient's head sufficient for each sensor 13 to detect brain activity of the patient when the patient wears the headgear 1.

After the gel is applied to the patient's scalp S, the second outer part 21b can be removed from the first inner part 21a. The second outer part 21b can then be thrown away or recycled for one-time use type application designs. Alternatively, the gel reservoir 23 of the second outer part 21b can be cleaned and/or sterilized and subsequently refilled with gel so that the second outer part can be connected to another first inner part 21a for repeat uses of the second outer part 21b in subsequent gel applications.

Repeat use application configurations for the second outer part 21b can include elements to facilitate a refilling of the gel reservoir 23 and/or the replacement of an emptied gel reservoir 23 with a new gel reservoir 23 (e.g. a gel reservoir 23 defined by a pouch 23b that is positionable within a gel reservoir opening, or chamber, defined by at least one sidewall 24 that helps define space for the gel reservoir 23). A gel reservoir pouch 23b can have an inner cavity or chamber defined therein to retain gel and include an outlet 61 that is in fluid communication with this gel fillable space so that the pouch is configured for connection to gel reservoir outlet 23a of the second outer part 21b, which can permit the gel to be passable from within the pouch 23b to the primary fluid conduit 25 for applying to at least one sensor 13 and head of a patient. To permit the gel reservoir pouch 23b to be removable and insertable into the second outer part 21b, the second outer part 21b can include an access panel 63 that is moveable or removable from the second outer part 21b to permit access to the gel reservoir 23 so a user can manipulate a gel reservoir pouch 23b for insertion, attachment, and/or removal.

Figure 12:
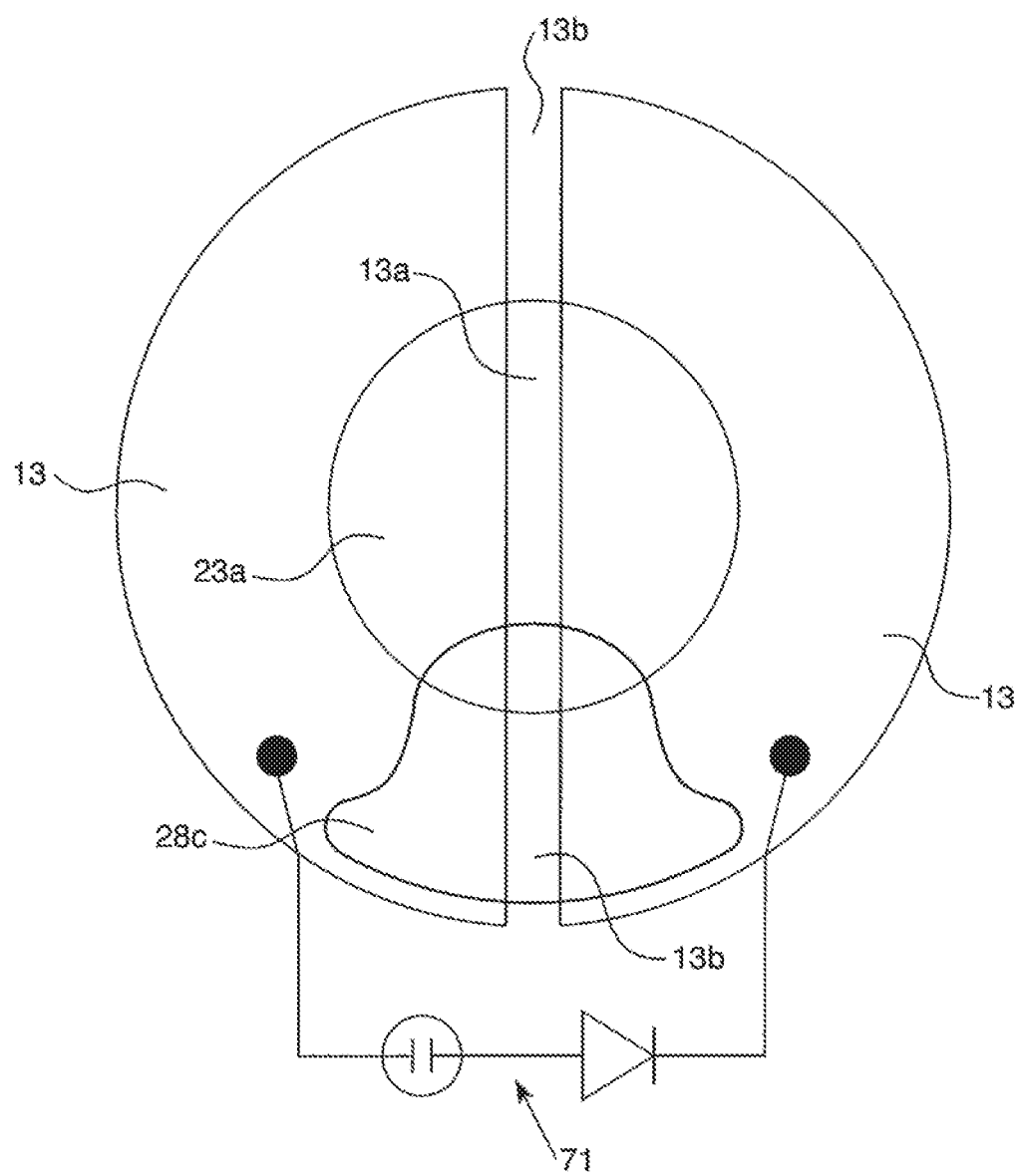
FIG. 12 is a schematic view of an exemplary gel filling detector that can be utilized in embodiments of the gel distribution modules shown in FIGS. 5-11.

One or more sensors 13 that can be positioned within the first inner part 21a can be configured to also provide a gel filling detection mechanism so that an indication can be provided to a user to indicate when the gel chamber 28c is filled sufficiently to provide an electrically conductive connection between one or more sensors 13 and the patient's head. For example, as shown in FIG. 12, the sensor 13 can be configured as two spaced apart sensor portions (e.g. a first sensor half and a second sensor half) that define a hole 13a or can be considered multiple spaced apart sensors 13 that define a gap 13b between the sensors 13.

The sensors 13 or sensor portions can be connected to a circuit 71 to facilitate detection of when the gel has sufficiently filled the gel chamber 28c. The circuit 71 can be positioned in the first inner part 21a that is attached to the body 2 adjacent the one or more sensors 13. The circuit 71 can be configured so that a bridge of the circuit will connect the multiple spaced apart sensors 13 or sensor portions after the gel from the gel reservoir 23 has passed from the first primary gel conduit 25 to sufficiently fill the gel chamber 28c so that the circuit 71 is completed via the gel within the gel chamber 28c. The completion, or connection of the circuit 71 provided by the gel filling the gel chamber 28c can provide feedback via an electrical signal to an indicator that is positioned on the gel distribution module. For example, a light emitting diode (LED) or speaker connected to circuit 71 that is positioned adjacent the external surface of the body 2 can be connected to the circuit 71 so that a user can see a colored light emitted from the LED and/or hear an audible indicator emitted from the speaker to indicate the gel has sufficiently filled the gel chamber 28c. Such an indicator can be connected to the first inner part 21a and/or the second outer part 21b.

FIGS. 14-21 illustrate yet additional exemplary embodiments of gel distribution modules 21 that can be utilized in embodiments of headgear 2 by being incorporated into the body 2 of the headgear in a location that is at or adjacent a sensor 13 positioned on an inner surface 7b of the headgear 1 for contact with the head of a patient wearing the headgear 1 (e.g. via sonic welding, sewing, or other attachment mechanism).

For example, the gel distribution modules 21 shown in FIGS. 14-17 can be incorporated into embodiments of the headgear (e.g. as may be appreciated from FIG. 13) via attachment to the body 2 of the headgear 1. The attachment of the gel distribution modules 21 to the body 2 of the headgear 1 can be provided by any number of attachment mechanisms (e.g. sonic welding, sewing, adhesion, interlocking connections, fastener profiles for attachment to body 2, etc.).

The first inner part 21a can be integral with the second outer part 21b via a molding operation or other attachment mechanism (e.g. welding, bonding, etc.). The second outer part 21b can be configured as a flexible or resilient body that defines a bladder in which gel can be retained between the first inner part 21a and second outer part 21b. The first inner part 21a can be configured as a plate or plate-like member configured for attachment to the body 2 of the headgear 1. For instance, the first inner part 21a can be welded via a sonic welded joint 21w or other attachment mechanism to the body 2 of the headgear at a location that is relatively coincident in location to a respective one of the sensors 13 of the sensor array of the headgear 1.

In some embodiments, the first outer part 21a can be formed of a polymeric material or other material that is more rigid than the second outer part 21b. For example, the first inner part can be composed of polyethylene (e.g. high density polyethylene, low density polyethylene, etc.), polycarbonate, polyvinyl chloride, or other type of plastic or polymeric material. The second outer part 21b can be configured as a resilient or flexible body that can permit the gel reservoir 23 defined by the first inner part 21a and second outer part 21b to be flexible. In some embodiments, the second outer part 21b can be structured as a blister or flexible dome or hemisphere.

In some embodiments, the second outer part 21b can have a body that is composed of layers of laminate material and metal foil to provide a flexible body, may be composed of an elastomeric material having a pre-selected durometer range to provide its flexible body, may be a thermoformed polymeric material formed to a pre-selected shape for defining the flexible outer portion of the reservoir 23 of the gel distribution module 21, may be a blow molded structure composed of a polymeric material, or may be a structure formed from a polymeric material or a composite material so that the second outer part 21b is more flexible than the first part 21a due to a difference in geometry of the part, thickness, shape, and/or material composition.

The second outer part 21b can have a solid exterior surface that allows the reservoir 23 to be defined to retain gel within the reservoir 23. The second outer part 21b can be composed of a material that is translucent or clear in color to permit a user to see within the module to evaluate the amount of gel retainer therein. In other embodiments, the second outer part 21b can be opaque or have a non-clear color.

Figure 17:
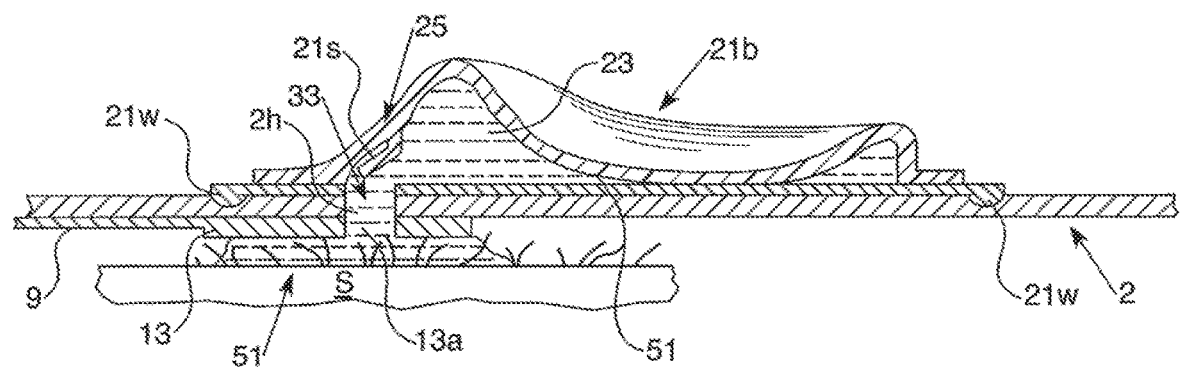
FIG. 17 is a cross-sectional view similar to FIG. 16 illustrating the exemplary gel distribution module in an actuated state in which gel has been output from the module and onto the head (e.g. scalp) of a patient.

The first inner part 21a can have a hole 33 that is aligned with a hole 2h in the body 2 of the headgear 1 located at or near a sensor 13 on the inner surface 7b of the headgear body. The hole 2h and hole 33 can also be aligned with an opening, inner hole, slot, or other type of aperture that can be defined in the body of the sensor 13 (e.g. hole 13a). The aligned holes 2h, 13a, and 33 can define at least part of the first primary gel conduit 25 along which gel may move for applying gel from the reservoir 23 onto the scalp S of a patient and the body of the sensor 13 to enhance the electrical connection the sensor may have with the patient's scalp or head. The motion of the gel 51 from the reservoir 23 to the scalp of a patient via the first primary gel conduit 25 can be actuated by a user pressing on the second outer part 21b to push the second outer part 21b sufficiently close enough to the first inner part 21a to cause a frangible or moveable seal member 21s to move from a closed position, which can also be referred to as a gel retention position (shown in FIG. 16), to an open position, which can also be referred to as a gel output position (shown in FIG. 17). The seal member 21s can be moveable between the retention (FIG. 16) and output (FIG. 17) positions so that the gel can be output from the reservoir via the holes 33, 2h, and 13a of the first primary gel conduit 25 for positioning gel onto the scalp S and body of the sensor 13 (e.g. as shown in FIG. 17, for example).

The seal member 21s can be a component of the first inner part 21a or second outer part 21b that is frangibly connected to one or both of these parts. The frangible connection can be defined so that the seal member 21s is separable from the first inner part 21a or the second outer part 21b to move from the retention position to the output position due to the force exerted by a user pressing on the second outer part 21b and the resultant pressure increase within the reservoir 23 caused by that force. The connection between the seal member 21s and the first inner part 21a or second inner part 21b can be defined so that a portion of the seal member 21s separates from the first inner part or the second outer part so the seal member 21s can be moved from the retention position to the output position by a flow of the gel that is driven by the force exerted by the user on the second outer part 21b. After the gel passes through the opening created by motion of the seal member 21s to its open position, the gel can pass along other portions of the primary gel conduit 25 via holes 33, 2h, and 13a onto the sensor body and patient scalp.

For embodiments where the connection the seal member 21s has to the second part 21b is to be separated, the seal member 21s may pivot about its connection with the first inner part 21a so its distal free end moves closer to the first inner part 21a (and also away from the second outer part 21b). For embodiments where the connection the seal member 21s has to the first part 21a is to be separated, the seal member 21s may pivot about its connection with the second outer part 21b so its distal free end moves closer to the second outer part 21b and away from the first inner part 21a.

In yet other embodiments, the seal member 21s can be configured to separate from both the first inner part 21a and the second outer part 21b. For such embodiments, the seal member 21s can be sized to pass through holes 33, 2h, and 13a so that the seal member can be output from the gel distribution module during the output of gel from the reservoir and onto the patient scalp and sensor body via the primary gel conduit 25.

It should be appreciated that for the one or more frangible connections that the seal member 21s may have to the first inner part 21a and/or second outer part 21b, the connection can be designed and configured to only permit a separation after a force is exerted on the seal member's connection that exceeds a predetermined threshold force. Such a threshold can be designed to avoid accidental or unintended actuation of the gel distribution module 21 for moving the seal member 21s to its open position to minimize incidents where a user may accidentally distribute gel at an undesired time.

The seal member 21s can be a component of the gel distribution module 21 that is formed when the module is molded or formed such that the seal member 21s is positioned between the first inner part 21a and second outer part 21b to help define a part of the gel reservoir 21 so that the seal member 21s is between the hole 33 and the gel reservoir 23 (e.g. via a molding operation, via injection molding, etc.). The one or more frangible connections that the seal member 21s can have to the first inner part 21a and/or second outer part 21b can be defined via the molding operation used to form the gel distribution module 21. In other embodiments, the seal member 21s can have its frangible connection(s) formed via welding, bonding, or other attachment mechanism that may meet a particular set of design and/or manufacturing criteria.

Figure 18:
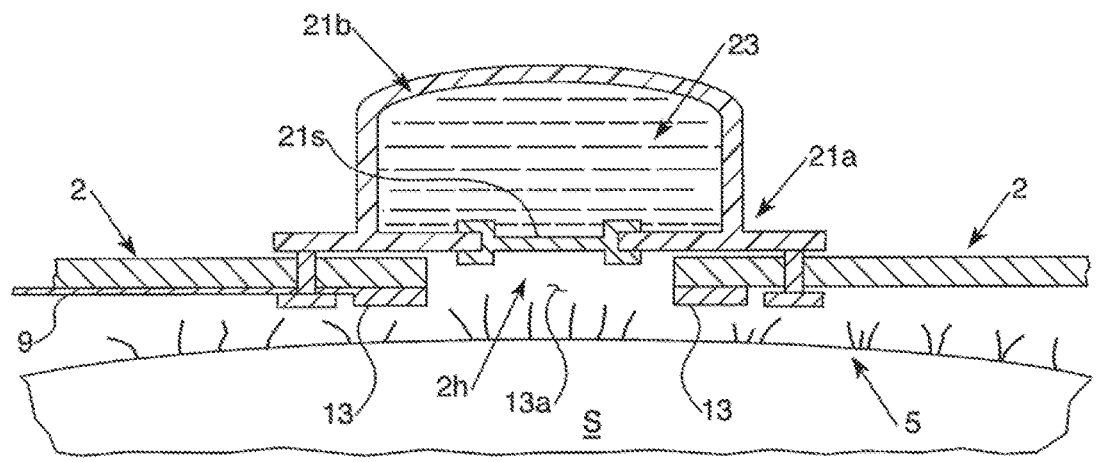
FIG. 18 is a cross-sectional view similar to FIG. 16 of another exemplary embodiment of a gel distribution module that can be utilized in embodiments of the headgear in a filled, non-actuated state, or position.
Figure 19:
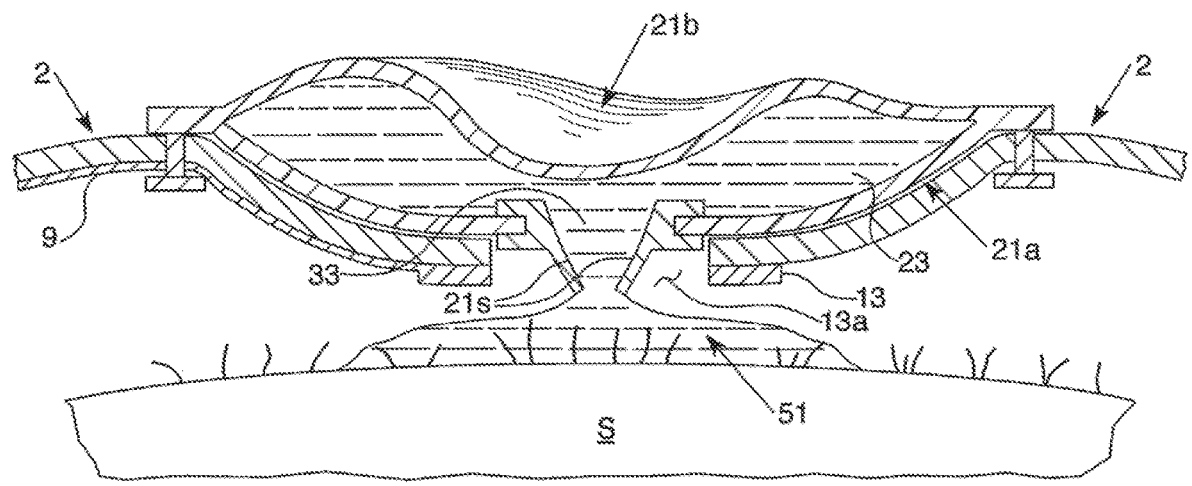
FIG. 19 is a cross-sectional view similar to FIG. 18 of the exemplary gel distribution module in an actuated state in which gel has been output from the module and onto the head (e.g. scalp) of a patient.

Embodiments of the gel distribution modules 21 shown in FIGS. 18-19 can also (or alternatively) be incorporated in embodiments of the headgear 1 (e.g. as may be appreciated from FIG. 13). It should be appreciated that the attachment of the gel distribution modules 21 to the body 2 of the headgear 1 can be provided by any number of attachment mechanisms (e.g. sonic welding, sewing, adhesion, interlocking connections, fastener profiles for attachment to body 2, etc.).

As can be appreciated from FIGS. 18 and 19, the seal member 21s can be positioned so that it is only attached to the first inner part 21a and has one or more frangible connections to the first inner part 21a or has an inner frangible portion that can permit the seal member 21s to be broken into multiple separate pieces that may move about connections the portions has with the first inner part to create a hole 33 that is in communication with the gel reservoir 23 to permit the gel to be output from the reservoir. The seal member 21s can be structured so it may be opened to define hole 33 in the first inner part 21a in response to an application of a force exerted by a user on the second outer part 21b that exceeds a pre-selected threshold force value or pressure value so that an opening for the gel reservoir 23 can be created that permits gel to be expelled out of the reservoir 23 and through holes 2h and 13a for application onto the scalp S and sensor 13. The movement of the seal member 21s via the actuation force provided by a user can move the seal member 21s from a closed position to an open position.

For the embodiment shown in FIGS. 18 and 19, the seal member 21s can be considered a portion of the floor of the gel reservoir 23 that is defined by the first inner part 21a that is configured to be broken or opened via application of a user exerted force on the second outer part 21b to increase the pressure within the reservoir 23 to a level that exceeds a pre-selected threshold to break away from the first inner part via one or more frangible connections or joints for defining a hole 33 in the first inner plate 21a. The first inner part 21a can be welded via at least one sonic welded joint 21w to the body 2 of the headgear or may be attached via other means or mechanisms (e.g. sewing, clips, rivets, other type of fastener, bonding, etc.).

For the embodiment shown in FIGS. 18 and 19, it should be appreciated that the seal member 21s can be configured so that it its frangible into multiple independently moveable parts that each move relative to a connection that portion has to the first inner part 21a to form the hole 33 after the seal member 21s fragments or fractures in response to the user applied actuation force. Alternatively, the seal member 21s can be configured to be separated from a portion of the first inner part 21a via at least one frangible connection to the first inner part 21a so that the seal member 21s is moveable to form the hole 33.

Figure 20:
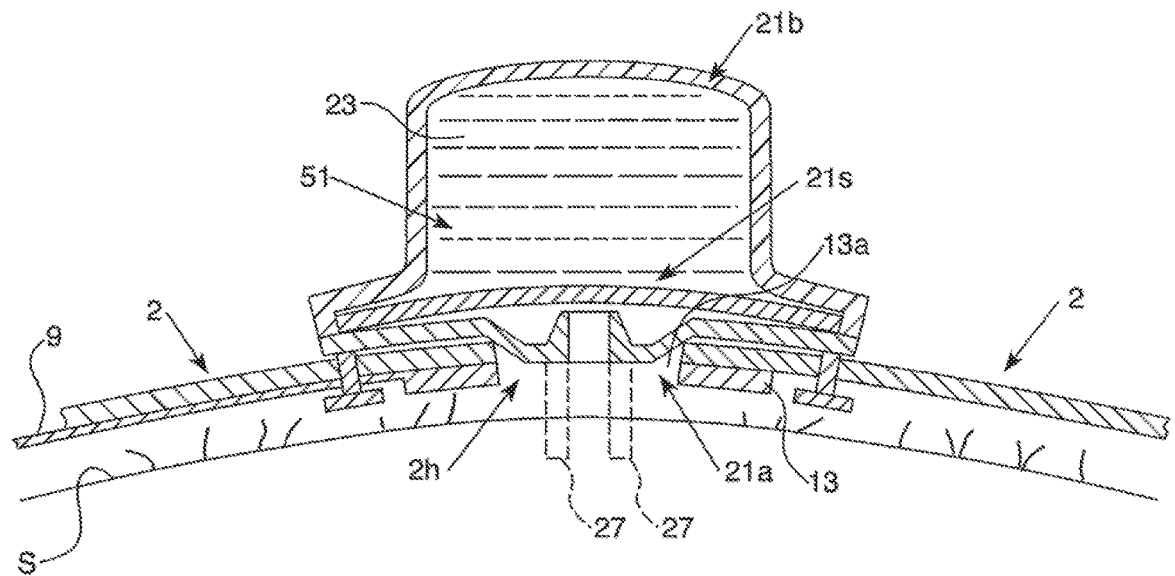
FIG. 20 is a cross-sectional view similar to FIGS. 16 and 18 of yet another exemplary embodiment of a gel distribution module that can be utilized in embodiments of the headgear 1 in a filled, non-actuated state, or position.
Figure 21:
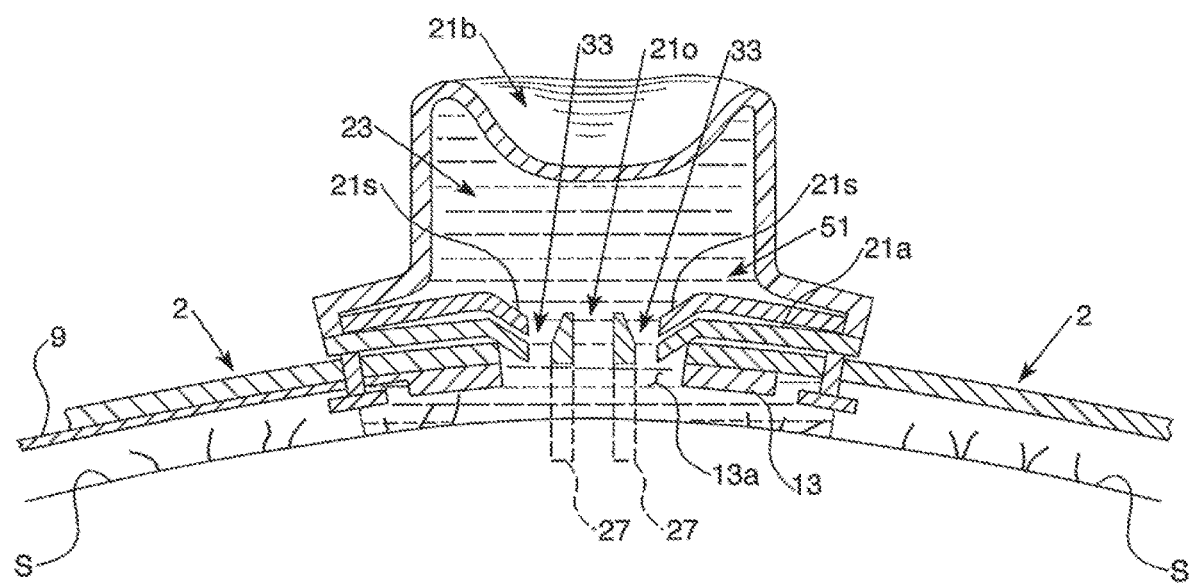
FIG. 21 is a cross-sectional view similar to FIG. 20 of the exemplary gel distribution module in an actuated state in which gel has been output from the module and onto the head (e.g. scalp) of a patient.

Embodiments of the gel distribution modules 21 shown in FIGS. 20-21 can also (or alternatively) be incorporated in embodiments of the headgear 1 (e.g. as may be appreciated from FIG. 13). It should be understood that the attachment of the gel distribution modules 21 to the body 2 of the headgear 1 can be provided by any number of attachment mechanisms (e.g. sonic welding, sewing, adhesion, interlocking connections, fastener profiles for attachment to body 2, etc.).

For the embodiment shown in FIGS. 20-21, the seal member 21s can be considered a portion of the floor of the gel reservoir 23 that extends from one side of the second outer part 21b to a second side of the second outer part 21b to define a floor or wall of the gel reservoir 23 so that the gel reservoir is defined by the second outer part 21b and the seal member 21s. The seal member 21s can be positioned between the hole 33 and the gel within the gel reservoir 23 so that the reservoir holds and retains the gel until the seal 21s is fractured, fragmented, or is partially separated from the second outer part 21b for movement from the closed position to the open position.

As can be appreciated from the above, the seal member 21s can be configured to be broken or opened via application of a user exerted force on the second outer part 21b to increase the pressure within the reservoir 23 to a level that exceeds a pre-selected threshold to cause a middle or center portion of the seal member 21s to fracture so the seal member 21s is separated into at least 2 portions that move away from each other to define an opening 210 in the reservoir 23 through which gel can pass out of the reservoir and through holes, 33, 2h, and 13a for applying the gel onto the scalp S and sensor 13. It should be appreciated that the seal member 21s can be configured so that it its frangible into multiple independently moveable parts that each move relative to a connection that the portion has to the second outer part 21b to form the gel reservoir output opening 210 after the seal member 21s fragments or fractures in response to the user applied actuation force. Alternatively (or additionally), the seal member 21s can be configured to be separated from a portion of the second outer part 21b via at least one frangible connection to the second outer part 21b so that the seal member 21s is moveable to the open position to form the gel reservoir output opening 210 in response to the user applied actuation force.

In the embodiment shown in FIGS. 20-21, the seal member 21s can be positioned so it is fully within the enclosure provided by the second outer part 21b and is between the second outer part 21b and the first inner part 21a to define the gel reservoir 23 with the second outer part. For such a configuration, the first inner part may not define the gel reservoir 23, but may at least partially define the primary gel conduit 25 through which the gel passes due to the user applied actuation force after the seal member 21s is moved to the open position (e.g. via fracture or via motion relative to the second outer part 21b via at least one frangible connection between the second outer part 21b and the seal member 21s breaking).

As discussed herein, the gel distribution module 21 can also have at least one projection 27 or multiple projections 27 (e.g. shown in broken line in FIG. 20). The projections 27 can be attached to the seal member 21s and/or the first inner part 21a. Each projection 27 can have a distal end 27a that can contact a scalp S so that a user can manipulate the gel distribution module to move the projection 27 so the distal end 27a is moved along the scalp S to directly contact the scalp S to abrade the skin of the scalp to help roughen the scalp surface. Such abrasion can improve the electrical connection the sensor 13 can have to the head of the patient after the gel is output from the gel reservoir 23 and onto the sensor 13 and scalp S.

It should be appreciated that embodiments of the body 2 can be structured to adjustably accommodate different sized heads of a user. For example, the body 2 having sensors 13 printed thereon or integral therein may be less flexible than an elastic mesh or elastomeric type cap. The body may therefore have difficulty being stretched to accommodate larger heads if the body 2 is not sufficiently sized for a larger head 2. To fit smaller heads, the body 2 can be configured to have outer peripheral portions that may be easily separated from the body These outer peripheral portions would not typically include sensors 13 to avoid loss of higher cost components of the headgear 1.

For example, the body 2 could include at least one frangible peripheral portion that extends along a perimeter of the body and is separable from a main body. There may also be one or more outer secondary frangible peripheral portions attached to the main body. The first primary frangible portion can be located between the one or more secondary frangible outer portions and the main portion.

Each frangible portion can be defined by a particular stitch connection that facilitates an easy removal of the frangible portion from the main body and/or inner frangible portion to which it is attached. The frangible portions can be alternatively provided by a releasable connection mechanism positioned along the periphery of the main portion or other frangible portion to which it is directly attached. Such a releaseable connection mechanism can include snaps, at least one zipper connection, or a connection mechanism utilizing a plurality of hook and loop fasteners (e.g. a Velcro connectors, etc.). For hook and loop fastener connections, the outer frangible portion can have a strip of hooks or loops and the inner portion or main part of body 2 can have the other of the strip of hooks or strip of loops for use of the hook and loop fastener mechanism.

In other embodiments, it is contemplated that the body 2 can be overmolded or otherwise attached to a cap so that the body lines the inner side of the cap. The gel distribution modules can then be attached to the body adjacent the sensors 13 to form the sensor hubs 41 so that the second outer parts 21b are outside of the cap and the inner first parts are inside the cap. The body 2 may be attached to the cap when the cap is kept is an extended or stretched state for some embodiments in which the body 2 itself does not fully define the cap structure. Such a connection can be an alternative to use of fungible portions that may permit a more flexible cap to be used to accommodate a larger range of sized heads when the body is composed of a material that has less flex capacity than may be needed to accommodate such a larger size range while still utilizing the sensor array 12 that is integral to the body 2 and the separate gel distribution modules 21 that are attachable to the body.

The gel distribution module 21 can also be configured to facilitate use of radio frequency identification (RFID) technology. Alternatively, or in addition, an RFID circuit can be positioned integral with the body 2. A power source for the RFID circuit can be connected to the circuit via a module having a power source that is configured for connection to the RFID circuit. The structure of such a power module can be similar to the gel distribution module, but instead of retaining gel, the module may be sized to retain a battery or a solar cell. As another option, the gel distribution module can also include a batter retaining portion for retaining a battery for connecting the battery to the RFID circuit defined on the body 2.

Embodiments of the body 2 having conductive connectors 9 and sensors 13 can also be configured to facilitate a detection of an asymmetric position of the headgear 1 on a patient's head. For example, left side conductive connectors 9 that each extends from the rear 2b of the body 2 to a sensor 13 on a left side of the body 2 can have a particular shape or configuration as it extends (e.g. a particular sinusoidal shape, etc.). The right side conductive connectors 9 that each extends from the rear 2b of the body 2 to a sensor 13 on a right side of the body 2 can also have a particular corresponding shape or configuration to the left side conductive connectors as it extends (e.g. a particular sinusoidal shape, etc.). The impedance of each conductive connector 9 may change due to the degree to which the shape of that conductive connector 9 changes when the body 2 is flexed into a headgear position and further stretched when positioned on a patient's head to be worn by the patient. If the left and right side corresponding conductive connectors have a significant difference in impedance (e.g. a difference that exceeds a pre-selected threshold or is at or exceeds such a threshold) this can indicate that one side is stretched more than another and that the headgear is not symmetrically positioned on the patient's head. An impedance measurement circuit can be defined on the body to measure the impedance and actuate an LED attached to the housing of a gel distribution module or other module having a similar structure without including a gel reservoir but instead retaining the LED. The LED can be connectable to the impedance measurement circuit of the body so it can emit a light when an asymmetric position of the left and right side sensors 13 is detected due to the impedance difference that is detected.

Embodiments of the body 2 can be used to form headgear 1 that is to be worn by a patient to help diagnose a medical condition of the patient. After the body 2 is adjusted into a desired shape for forming headgear 1, the body 2 can have different portions connected together to maintain the body in the desired shape via sewing, sonic welding, stapling, or other attachment mechanism. In other embodiments, the body 2 may not have different portions attached together after being adjusted into its desired shape for the headgear. Instead, a patient's head can be inserted into the formed opening 1a of the headgear. Gel distribution modules 21 and/or other modules (e.g. power module, etc.) can be attached to the body 2 prior to the body being formed into headgear 1 or shaped to define the headgear 1, or after the body is adjusted into the headgear shape.

After the patient's head is inserted into opening 1a of the headgear 1, the patient's ears can be passed through the ear holes 5a (or holes 2w) on the left and right sides of the headgear defined by the body 2 when the headgear is being worn on the patient's head. The communication connector 11 can be connected to the computer device and/or a transceiver element or other mechanism for connection to a computer device after the patient is wearing the headgear or prior to the patient wearing the headgear.

Once the headgear 1 is on the patient's head, the headgear 1 can be adjusted into a desired position in which the sensors 13 of the sensor array 12 are symmetrically positioned. Then, the headgear 1 can be tightened onto the patient's head via chin strap(s) 3 and/or circumferential tightening provided via a drawstring or other cords attached to the left and right side portions 5. In some embodiments, the headgear may be partially tightened, then re-positioned to provide an improved symmetrical positioning of the sensors 13 before being further tightened. The assessment of the proper positioning of the sensors 13 of the sensor array can include, for example, via positional assessments that verify a sufficient symmetrical position of the sensors and that a sufficient number of the sensors have an acceptable connection to the head of the patient. It is also contemplated that the headgear may be tightened, then loosened for repositioning on the patient's head before being tightened a second time after that repositioning of the headgear. Gel can be distributed onto the patient's head after the headgear is in a desired position on the patient's head to help improve the connection between sensors 13 and the patient's head to facilitate the sensors' ability to measure a condition of the patient. Supplemental gel can also be distributed (e.g. injected, applied, etc.) onto the patient's head if more gel is determined to be needed after an initial distribution of gel. After the gel is distributed and the headgear and sensors are in a desired position, the sensors 13 can be in direct contact with the patient's scalp S or can be positioned to be in direct contact with at least the gel, which may be located between the sensors 13 and the scalp S of the patient. Thereafter, the headgear can be used in testing of the patient for diagnosing a medical condition of the patient.

For some embodiments, after testing the headgear 1 having the gel distribution modules 21 can be thrown away. Such embodiments may utilize a headgear 1 designed and configured for a single use.

In other embodiments, after testing, the modules (e.g. gel distribution modules 21, power modules, etc.) can be removed from the headgear 1 via the snap-connections, by breaking off the first inner part 21a from the second outer part 21b, or via another type of releasement mechanism or separation process. These modules may then be thrown out or recycled. The body 2 can then be cleaned so that any gel is removed from the body 2. The removal of the gel can help avoid the sensors 13 being corroded from prolonged exposure to the gel, for example. In some embodiments, it is contemplated that embodiments of the body 2 without modules attached to it can be washed via a washing machine or other washing tool. After washing, the body 2 could be re-used to form headgear 1 for use on a new patient. New gel distribution modules 21 and/or power modules could be attached to the body 2 for such a use.

It should be appreciated that different embodiments of an electrode array, electrode headgear, neurological condition detection device can utilize different arrangements to meet a particular set of design criteria. For instance, the sensors 13 can have bodies of different shapes (e.g. polygonal shaped, oval shaped, etc.) and can have only one inner hole 13a or have more than one such hole 13a. As another example, the size, shape, and configuration of the conductive connectors 9 can be different from the exemplary arrangements shown in FIGS. 1 and 2. As yet another example, the arrangement, size, and sensor density of the sensor array 12 can be adjusted to meet a particular set of design criteria.

As yet another example, the size and shape of the fabric body 2 can be adjusted to meet a particular set of design criteria. For instance, the fabric composition of the body can utilize a different material (e.g. a mix of cotton and polyester threads, acrylic threads, acetate threads, nylon threads, combinations of these types of threads, or other fabric material). The weaving, knitting, or other fabrication method used to form the body 2 can also be any suitable type of method. The type of loom used (e.g. air jet, rapier, etc.) and/or the fabrication method employed can be any suitable method for forming the body 2. In some embodiments, it is contemplated that the body can be composed of other materials, such as rubber or latex rubber in which a sheet of the material is cut to form the body 2 (e.g. the body 2 may not be woven or knitted fabric).

As yet another example, it should be appreciated that some components, features, and/or configurations may be described in connection with only one particular embodiment, but these same components, features, and/or configurations can be applied or used with many other embodiments and should be considered applicable to the other embodiments, unless stated otherwise or unless such a component, feature, and/or configuration is technically impossible to use with the other embodiment. Thus, the components, features, and/or configurations of the various embodiments can be combined together in any manner and such combinations are expressly contemplated and disclosed by this statement. Therefore, while certain exemplary embodiments of headgear, electrodes, sensor arrays, sensor hubs, gel distribution mechanisms, neurological condition detection mechanisms, and methods of making and using the same have been shown and described above, it is to be distinctly understood that the invention is not limited thereto but may be otherwise variously embodied and practiced within the scope of the following claims.

What is claimed is:

1. Headgear for detection of a neurological condition of a patient, comprising:
a flexible body having an array of sensors including a plurality of sensors defined thereon and a plurality of conductive connectors defined thereon, each of the conductive connectors extending from a respective one of the sensors for connection of the sensors to a computer device;
a plurality of gel distribution modules, each gel distribution module attached to the flexible body adjacent a respective one of the sensors of the sensor array;
each of the gel distribution modules comprise a first inner part that is connectable to a second outer part, the first inner part being attached to the flexible body, the first inner part being connected to the second outer part such that the first inner part is positioned between the respective one of the sensors to which the gel distribution module is adjacently positioned and the second outer part;
each of the gel distribution modules having a gel reservoir at least partially defined via the second outer part, the second outer part structured as a flexible blister, a flexible dome, or a flexible hemisphere, the second outer part being flexible so that the second outer part is more flexible than the first inner part such that the second outer part is flexibly moveable to change a dimension of the gel reservoir to increase a pressure within the gel reservoir to exceed a pre-selected threshold for outputting of gel from the gel reservoir to a scalp of the patient wearing the headgear via at least one hole of the first inner part that is a portion of a primary gel conduit of the first inner part along which the gel moves as it is expelled from the gel reservoir to be applied onto the scalp; and
the first inner part having at least one gel aperture in communication with the primary gel conduit such that a portion of the gel is passable from the primary gel conduit to the at least one gel aperture to facilitate formation of an electrical connection between the respective sensor to which the gel module is adjacently positioned and the scalp, the gel aperture extending away from the primary gel conduit such that the portion of the gel passed to the at least one gel aperture flows in a flow direction that differs from a flow direction along which the gel passes as the gel flows through the primary gel conduit for contact with the scalp.

2. The headgear of claim 1, wherein each of the gel distribution modules include a seal member connected to at least one of the first inner part and the second outer part, the seal member configured to move from a closed position to an open position in response to the pressure within the gel reservoir increasing to exceed the pre-selected threshold for outputting of the gel from the gel reservoir.

3. The headgear of claim 2, wherein each of the gel distribution modules has at least one projection that extends away from the first inner part to contact a head of the patient when the patient wears the headgear.

4. The headgear of claim 3, wherein each gel distribution module is attached to the flexible body such that the gel distribution module is manipulatable to move the at least one projection along the head of the patient to abrade skin on the scalp of the patient.

5. The headgear of claim 2, comprising, at least one light emitting diode, each light emitting diode connectable to respective one of the gel distribution modules, each light emitting diode configured to emit a light to indicate the respective sensor of the sensor array to which the gel distribution module is positioned adjacent has a sufficient connection to a head of the patient for use in testing of the patient.

6. The headgear of claim 2, comprising, at least one light emitting diode connectable to at least some of the conductive connectors to emit a light in response to an impedance difference between the conductive connectors to which the light emitting diode is connected is at or exceeds a pre-selected threshold to indicate an asymmetric positioning of the sensors of the headgear on a head of the patient.

7. Headgear for detection of a neurological condition of a patient, comprising:
a flexible body having a sensor array including a plurality of sensors defined thereon and a plurality of conductive connectors defined thereon, each of the conductive connectors extending from a respective one of the sensors for connection of the sensors to a computer device; and
a plurality of gel distribution modules, each gel distribution module attached to the flexible body adjacent a respective one of the sensors of the sensor array;
wherein each of the gel distribution modules comprise a first inner part that is connectable to a second outer part, the first inner part being positioned on an interior facing surface of the flexible body and the second outer part being positioned on an exterior facing surface of the flexible body that is opposite the interior facing surface of the flexible body, the first inner part being connected to the second outer part such that the respective one of the sensors to which the gel distribution module is adjacently positioned is between the first inner part and the second outer part; and
wherein the first inner part has a recess and a gel distributor element that extends from the recess to a position that partially fills a primary gel conduit to direct a portion of gel that passes through the primary gel conduit into a gel chamber that is at least partially defined by the recess of the first inner part, at least a portion of the respective sensor of the sensor array to which the gel module is adjacently positioned being positioned adjacent the recess such that gel that is passed within the gel chamber via the gel distributor element contacts the respective sensor of the sensor array to which the gel module is adjacently positioned.

8. The headgear of claim 7, wherein the gel distribution module has a supplementary gel conduit that is at least partially defined by at least one hole in the second outer part that is spaced apart from the gel reservoir and is aligned with an opening of the first inner part, the opening of the first inner part being spaced apart from the hole of the first inner part that partially defines the primary gel conduit.

9. The headgear of claim 7, wherein the flexible body is comprised of fabric, polyester, cotton, polyester blended fabric, polyester threads, nylon, flax, rayon, viscose, material composed of regenerated cellulose fibers, wool, bamboo, texliner mesh, hemp, leather, fish leather, lyocell, or a textile material.

10. The headgear of claim 7 wherein the flexible body has a front side, a rear side opposite the front side, a left side, and a right side opposite the left side, and the sensors are defined on the front side, the rear side, the left side and the right side via screen printing or membrane overlaying.

11. The headgear of claim 7, wherein the flexible body includes at least one frangible peripheral portion that is releaseable from a main inner portion.

12. The headgear of claim 11, where the at least one frangible peripheral portion is attached via a loop and hook connector, snaps, or a stitched connection.

13. Headgear for detection of a neurological condition of a patient, comprising:
   a flexible body having a plurality of sensors defined thereon and a plurality of conductive connectors defined thereon, each of the conductive connectors extending from a respective one of the sensors for connection of the sensors to a computer device; and
   a plurality of gel distribution modules, each gel distribution module attached to the flexible body adjacent a respective one of the sensors of the sensor array;
   each of the gel distribution modules comprise a first inner part that is connectable to a second outer part, the first inner part being attached to the flexible body, the first inner part being connected to the second outer part such that the first inner part is positioned between the respective one of the sensors to which the gel distribution module is adjacently positioned and the second outer part;
   each of the gel distribution modules having a gel reservoir at least partially defined via the second outer part and a seal member, the second outer part structured as a flexible blister, flexible dome, or flexible hemisphere the second outer part being flexible so that the second outer part is more flexible than the first inner part such that the second outer part is flexibly moveable to change a dimension of the gel reservoir to increase a pressure within the gel reservoir to exceed a pre-selected threshold for outputting of gel from the gel reservoir to a scalp of the patient wearing the headgear via at least one hole of the first inner part that is a portion of a primary gel conduit along which the gel moves as it is expelled from the gel reservoir to be applied onto the scalp; and
   the seal member connected to at least one of the first inner part and the second outer part, the seal member configured to move from a closed position to an open position in response to the pressure within the gel reservoir increasing to exceed the pre-selected threshold for outputting of the gel from the gel reservoir.

14. The headgear of claim 13, wherein one of:
   the seal member is only attached to the first inner part via at least one frangible connection for movement from the closed position to the open position;
   the seal member is only attached to the second outer part via at least one frangible connection for movement from the closed position to the open position;
   the seal member is attached to both the first inner part and the second outer part and has a frangible connection with at least one of the first inner part and the second outer part for movement from the closed position to the open position; and
   the seal member is configured to fracture into multiple pieces for movement from the closed position to the open position in response to the pressure of the gel reservoir exceeding the pre-selected threshold.

* * * * *